United States Patent [19]
Balkovec et al.

[11] Patent Number: 5,514,651
[45] Date of Patent: *May 7, 1996

[54] AZA CYCLOHEXAPEPTIDE COMPOUNDS

[75] Inventors: James M. Balkovec, North Plainfield; Frances A. Bouffard, Scotch Plains; James F. Dropinski, Piscataway, all of N.J.

[73] Assignee: Merck & Co., Inc., Rahway, N.J.

[*] Notice: The term of this patent shall not extend beyond the expiration date of Pat. No. 5,378,804.

[21] Appl. No.: 307,978

[22] Filed: Sep. 16, 1994

[51] Int. Cl.$^6$ .............................. A61K 38/12; C07K 7/64
[52] U.S. Cl. .................... 514/11; 514/9; 514/2; 530/317; 930/270; 930/DIG. 548; 930/DIG. 546
[58] Field of Search .................... 530/317; 514/11, 514/9; 930/270, DIG. 548, DIG. 546

[56] References Cited

U.S. PATENT DOCUMENTS

| | | | |
|---|---|---|---|
| 5,021,341 | 6/1991 | Giacobbe et al. | 435/71.1 |
| 5,378,804 | 1/1995 | Balkhovec et al. | 530/317 |

FOREIGN PATENT DOCUMENTS 561639  9/1993  European Pat. Off. .

OTHER PUBLICATIONS

Zanbias, Journal of Medicinal Chemistry, vol. 35, pp. 2843–2835 (1992).
Walzer, et al., Diagn. Microbiol. Infect. Dis., vol. 21, pp. 1–6, 1984.

Primary Examiner—Christina Y. Chan
Assistant Examiner—T. D. Wessendorf
Attorney, Agent, or Firm—Elliott Korsen; Mark R. Daniel

[57] ABSTRACT

The present invention relates to aza cyclohexapeptide compounds of the formula (Seq ID Nos. 1–10)

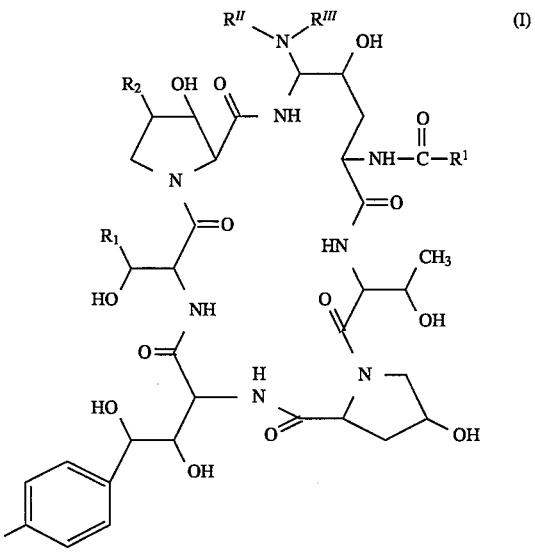

which may be useful as antibiotics, antifungal agents and for the treatment of *Pneumocystis carinii* infections.

5 Claims, No Drawings

AZA CYCLOHEXAPEPTIDE COMPOUNDS

BACKGROUND OF THE INVENTION

The present invention is directed to certain aza cyclohexapeptide compounds which may be useful as antifungal and antipneumocystis agents.

There presently exists a need for new antifungal and antipneumocystis compounds due to an increase in the number of isolates which are resistant to conventional agents. Additionally, conventional agents show somewhat high levels of toxicity which limit their usefulness. Lastly, the incidence of *Pneumocystis carinii* pneumonia is increasing, particularly in view of the high incidence of immunocompromised patients susceptible to infection, such as those with AIDS.

SUMMARY OF THE INVENTION

The compounds of the present invention, Compound I (Seq ID Nos. 1–10) are characterized in having a nitrogen attached to the cyclohexapeptide ring at the 5-carbon of the 4-hydroxyornithine component (hereinafter "C-5-orn") and may be represented by the formula

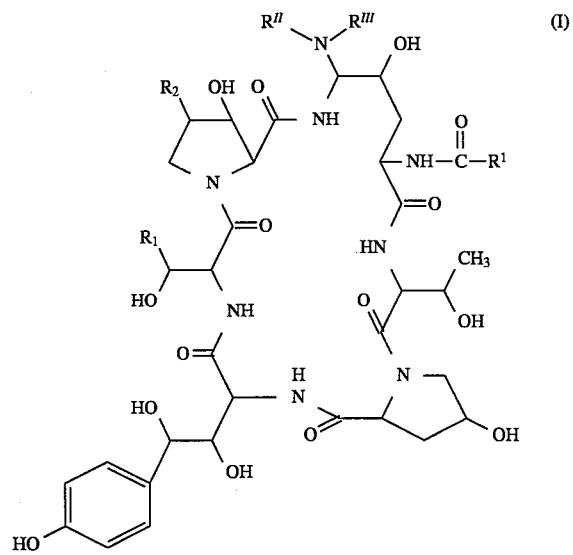

wherein
$R_1$ is $CH_3$, $CH_2CN$, $CH_2CH_2NH_2$ or $CH_2CONH_2$;
$R_2$ is H, $CH_3$ or OH;
$R^I$ is

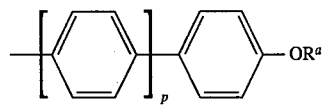

wherein
$R^a$ is $C_1-C_{10}$ alkyl; or $(CH_2)_q NR^b R^c$ wherein $R^b$ and $R^c$ are independently H, $C_1-C_{10}$ alkyl or $R^b$ and $R^c$ taken together with the nitrogen atom are

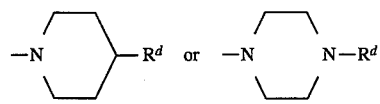

wherein
$R^d$ is $C_1-C_{16}$ alkyl, phenyl or benzyl.

$R^{II}$ is H, $C_1-C_4$ alkyl, $C_3-C_4$ alkenyl, $(CH_2)_{2-4}OH$, $(CH_2)_{2-4}NR^{IV}R^V$, $CO(CH_2)_{1-4}NH_2$;
$R^{III}$ is H, $C_1-C_4$ alkyl; or
$R^{II}$ and
$R^{III}$ taken together are $-(CH_2)_4-$, $-(CH_2)_5-$, $-(CH_2)_2O(CH_2)_2-$ or $-(CH_2)_2-NH-(CH_2)_2-$;
$R^{IV}$ is H or $C_1-C_4$ alkyl;
$R^V$ is H or $C_1-C_4$ alkyl;
p is 1,2 or 3;
q is 2 or 3 or 4 or
a pharmaceutically acceptable acid addition salt thereof.

Preferred embodiments of the invention are those of Compound (I) where
$R_1$ is $CH_2CH_2NH_2$,
$R_2$ is H,
$R^I$ is

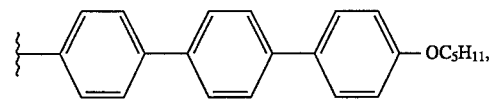

$R^{II}$ is $CH_2CH_2NH_2$, and
$R^{III}$ is H; or
$R_1$ is $CH_3$,
$R_2$ is $CH_3$,
$R^I$ is

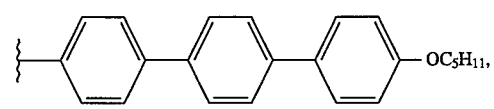

$R^{II}$ is $CH_2CH_2NH_2$, and
$R^{III}$ is H; or
$R_1$ is $CH_2CH_2NH_2$,
$R_2$ is H,
$R^I$ is

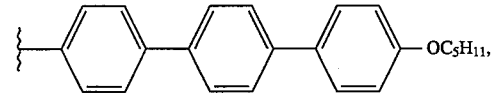

$R^{II}$ is $COCH_2NH_2$, and
$R^{III}$ is H; or
$R_1$ is $CH_2CH_2NH_2$,
$R_2$ is H,
$R^I$ is

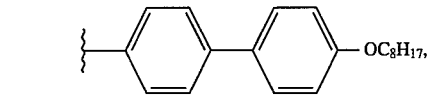

$R^{II}$ is $CH_2CH_2NH_2$, and
$R^{III}$ is H.

The compounds of this invention may be formulated into pharmaceutical compositions which are comprised of the compounds of formula I in combination with a pharmaceutically acceptable carrier.

The compounds of this invention are useful in treating fungal infections and for the treatment and prevention of infections caused by *Pneumocystis carinii* which are often found in immunocompromised patients such as, for example, those suffering with AIDS.

Throughout the specification and appended claims, a given s chemical formula or name shall encompass all optical and stereoisomers as well as racemic mixtures where such isomers and mixtures exist.

The term alkyl refers to straight, branched or cyclic chain hydrocarbon groups, e.g., methyl, ethyl, n-propyl, isopropyl, n-butyl, pentyl, hexyl, heptyl, cyclopentyl, cyclohexyl, cyclohexylmethyl and the like.

The term cycloalkyl refers to a species of alkyl containing from 3 to 15 carbon atoms without alternating or resonating double bonds between carbon atoms.

The term alkenyl refers to groups such as, e.g., vinyl, 1-propene-2-yl, 1-butene-4-yl, 2-buten-4-yl, 1-pentene-5-yl and the like.

The term alkoxy refer to straight or branched chain oxyalkyl groups such as, e.g., methoxy, ethoxy, butoxy, heptoxy, dodecyloxy, and the like.

The compounds of the present invention are generally obtained as mixtures of stereoisomeric forms in which one form usually predominates. Conditions may be adjusted by means within the normal skill of the skilled artisan to obtain predominantly the desired isomer. The compounds with preferred stereoisomeric form designated herein as the "normal" form are those in which the group at the "C-5-orn" position is below the plane at the said position. The designation "epi" has been employed for those compounds in which the group at the "C-5-orn" position is above the plane.

Pharmaceutically acceptable salts suitable as acid addition salts are those from acids such as hydrochloric, hydrobromic, phosphoric, sulfuric, maleic, citric, acetic, tartaric, succinic, oxalic, malic, glutamic and the like, and include other acids related to the pharmaceutically acceptable salts listed in *Journal of Pharmaceutical Science*, 66, 2 (1977).

The acyl substituent on the 4-hydroxyornithine nitrogen differs from natural products and known compounds in being an aromatic chain of at least two phenyl groups and further extended by substituents in the para position.

Representative nuclei for the aza derivatives of the present invention (Compound I) and the sequence ID for these compounds may be seen in the following table. Since the peptide nuclei would be the same irrespective of substituents R', R" or R''', and since the sequence identification number is assigned for the nuclear variations, the amines and salts have the same sequence ID's.

| Aza Compound | $R_1$ | $R_2$ | SEQ ID NO. |
|---|---|---|---|
| I-1 | $CH_2CONH_2$ | $CH_3$ | 1 |
| I-2 | $CH_2CN$ | $CH_3$ | 2 |
| I-3 | $CH_2CH_2NH_2$ | $CH_3$ | 3 |
| I-4 | $CH_3$ | $CH_3$ | 4 |
| I-5 | $CH_2CONH_2$ | H | 5 |
| I-6 | $CH_2CN$ | H | 6 |
| I-7 | $CH_2CH_2NH_2$ | H | 7 |
| I-8 | $CH_2CONH_2$ | OH | 8 |
| I-9 | $CH_2CN$ | OH | 9 |
| I-10 | $CH_2CH_2NH_2$ | OH | 10 |

The compounds are soluble in dower alcohols, and polar aprotic solvents such as N,N-dimethylformamide (DMF), dimethyl sulfoxide (DMSO) and pyridine. They are insoluble in solvents such as diethyl ether and acetonitrile.

The compounds of the present invention are useful as an antibiotic, especially as an antifungal agent or as an antiprotozoal agent. As antifungal agents they are useful for the control of both filamentous fungi and yeasts. They are especially adaptable to be employed for the treatment of mycotic infections in mammals, especially those caused by Candida species such as *C. albicans, C. tropicalis* and *C. pseudos-tropicalis*, Cryptococcus species such as *C. neoformans* and Aspergillus species such as *A. fumigatus, A. flavus, A. niger*. They are also useful for the treatment and/or prevention of *Pneumocystis carinii* pneumonia to which immune-compromised patients are especially susceptible as hereinafter described.

The structural aspects which distinguish the compounds of the present invention is the combination of a nitrogen attached to the cyclohexapeptide ring at the 5-carbon of the 4-hydroxyornithine compound and the side chain acyl group. For the desirable combination of properties, the amino acids of the nucleus are not changed.

The compounds of the present invention may be prepared from cyclopeptides having the formula

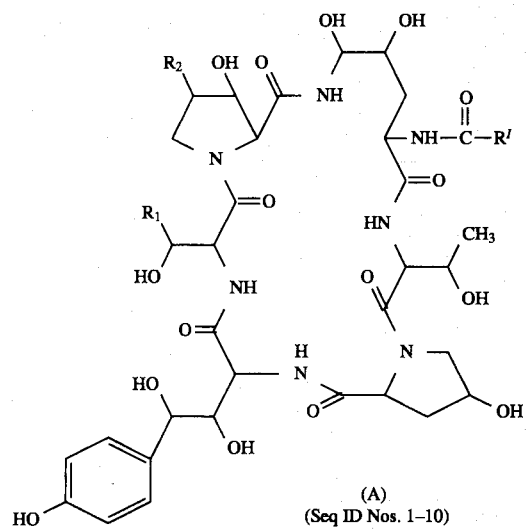

(A)
(Seq ID Nos. 1–10)

by a series of reactions in which the oxygen atom at the "C-5-orn" (which also may be referred to as the hemiaminal position) is ultimately replaced by nitrogen. The starting materials may be natural products or modified natural products as subsequently described.

The sequence IDs of the starting materials are seen in the following table:

| Compound | $R_1$ | $R_2$ | Starting Material SEQ ID NO. |
|---|---|---|---|
| A-1 | $CH_2CONH_2$ | $CH_3$ | 11 |
| A-2 | $CH_2CN$ | $CH_3$ | 12 |
| A-3 | $CH_2CH_2NH_2$ | $CH_3$ | 13 |
| A-4 | $CH_3$ | $CH_3$ | 14 |
| A-5 | $CH_2CONH_2$ | H | 15 |
| A-6 | $CH_2CN$ | H | 16 |
| A-7 | $CH_2CH_2NH_2$ | H | 17 |
| A-8 | $CH_2CONH_2$ | OH | 18 |
| A-9 | $CH_2CN$ | OH | 19 |
| A-10 | $CH_2CH_2NH_2$ | OH | 20 |

When in Compound A-1, $R_1$ is $CH_3$ or $-CH_2CONH_2$ they may be directly employed in the first method. When $R_1$ is $-CH_2CN$ or $-CH_2CH_2NH_2$, the group $-CH_2CONH_2$ may be first converted to $-CH_2CN$ or $-CH_2CH_2NH_2$ as subsequently disclosed, and all the modified compounds (Seq ID Nos. 12,13,16,17,19,20) used in the first method, or alternatively, a compound in which $R_1$ is $-CH_2CONH_2$ may be employed to produce a compound with N at the hemiaminal position, and the $-CH_2CONH_2$ of the resulting product then converted to $-CH_2CN$ or-$CH_2CH_2NH_2$.

First, when $R_1$, of the starting material is the same as that in the product, the following sequence may be employed:

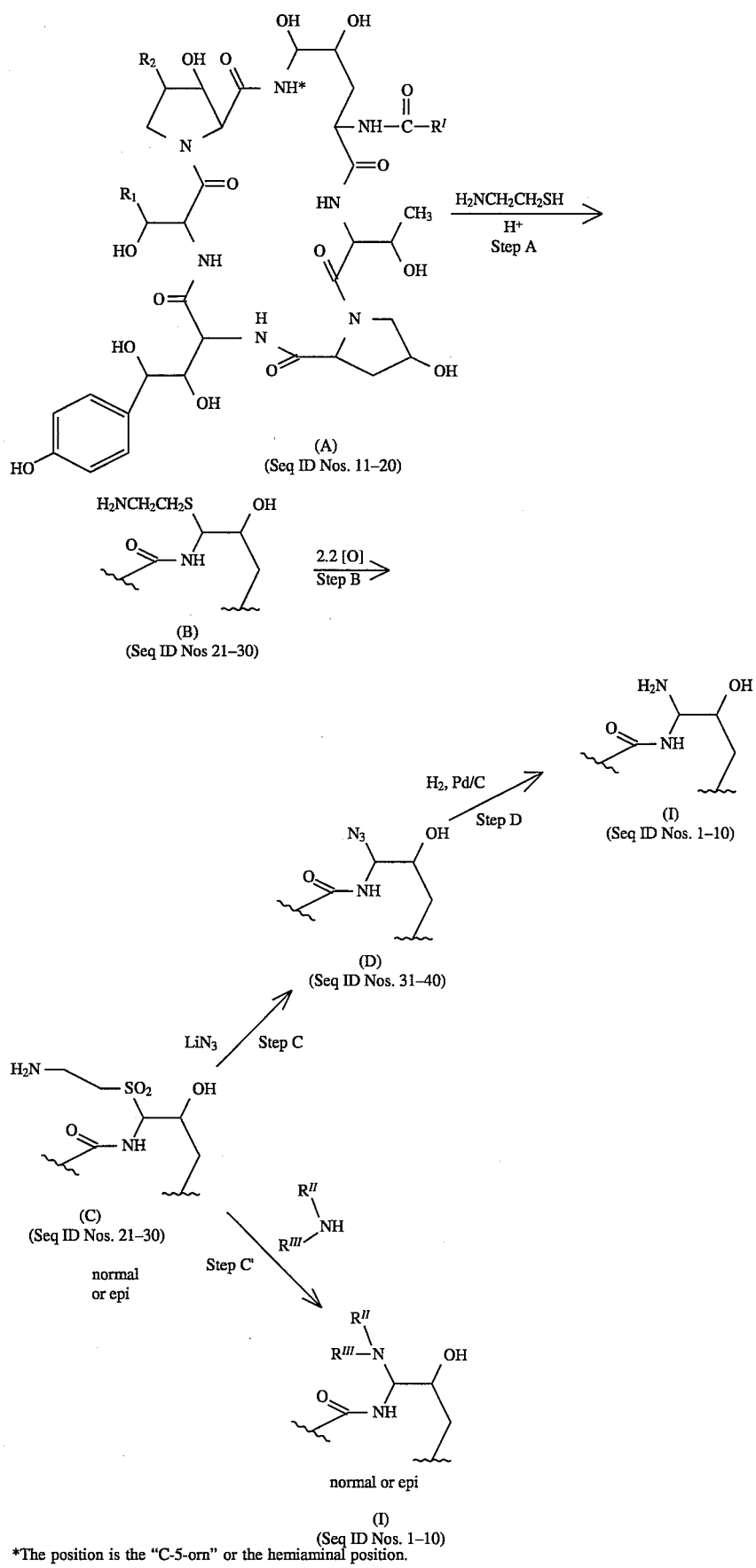
*The position is the "C-5-orn" or the hemiaminal position.

In Step A, the starting material Compound A (Seq ID Nos. 11–20), alkylthiol or arylthiol and acid am caused to react in an aprotic solvent under anhydrous conditions for time sufficient for reaction to take place with the formation of Compound B (Seq ID Nos. 21–30), seen in the following table. Aminoethanethiol has been found to be useful for this step.

| Compound | $R_1$ | $R_2$ | Sulfur Intermediate SEQ ID NO. |
| --- | --- | --- | --- |
| B-1 | $CH_2CONH_2$ | $CH_3$ | 21 |
| B-2 | $CH_2CN$ | $CH_3$ | 22 |
| B-3 | $CH_2CH_2NH_2$ | $CH_3$ | 23 |
| B-4 | $CH_3$ | $CH_3$ | 24 |
| B-5 | $CH_2CONH_2$ | H | 25 |
| B-6 | $CH_2CN$ | H | 26 |
| B-7 | $CH_2CH_2NH_2$ | H | 27 |
| B-8 | $CH_2CONH_2$ | OH | 28 |
| B-9 | $CH_2CN$ | OH | 29 |
| B-10 | $CH_2CH_2NH_2$ | OH | 30 |

For Step A, suitable acids include strong organic acid and mineral acids. Examples of strong organic acids are camphorsulfonic acid, p-toluenesulfonic acid and methanesulfonic acid. Mineral acids include hydrochloric acid and hydrobromic acid. Camphorsulfonic acid is preferred.

Suitable solvents include DMF, DMSO, 1-methyl-2-pyrrolidinone and hexamethyl phosphoric triamide (HMPA). DMF or DMSO is preferred.

The reaction is generally carried out at ambient temperature for from 1 to about 10 days.

In carrying out the reaction, the cyclohexapeptide compound, the thiol compound and acid are stirred together in a suitable solvent until the reaction is substantially complete. The reaction mixture then is diluted with water and flash chromatographed on reverse phase resins using 10 to 40 percent acetonitrile/water (containing 0.1% trifluoroacetic acid) as eluant. Trifluoroacetic acid may hereinafter be designated "TFA". The fractions containing the desired product may be concentrated and lyophilized and the lyophilized material purified by preparative high performance liquid chromatography (HPLC).

Appropriate columns for HPLC are commercially available columns sold under trade mark names or trade names such as "ZORBAX" (DuPont), "DeltaPak" (Waters), Bio-Rad (Bio-Rad), "LICHROPREP" RP18 (E. Merck). The specific columns are identified in the working examples.

In Step B, Compound C (Seq ID Nos. 21–30), a sulfone is obtained by the oxidation of Compound B. Suitable oxidizing agents or oxidants include "OXONE," ($KHSO_5 \cdot KHSO_4 \cdot K_2SO_4$ 2:1:1, Aldrich Chemicals) metachloroperoxybenzoic acid, and peroxyacetic acid. The sequence ID of Compound C is the same as that of Compound B since the atom attached to the hemiaminal carbon is still sulfur. Thus, the sequence IDs of the sulfones are as follows:

| Compound | $R_1$ | $R_2$ | Sulfone SEQ ID NO. |
| --- | --- | --- | --- |
| C-1 | $CH_2CONH_2$ | $CH_3$ | 21 |
| C-2 | $CH_2CN$ | $CH_3$ | 22 |
| C-3 | $CH_2CH_2NH_2$ | $CH_3$ | 23 |
| C-4 | $CH_3$ | $CH_3$ | 24 |
| C-5 | $CH_2CONH_2$ | H | 25 |
| C-6 | $CH_2CN$ | H | 26 |
| C-7 | $CH_2CH_2NH_2$ | H | 27 |
| C-8 | $CH_2CONH_2$ | OH | 28 |
| C-9 | $CH_2CN$ | OH | 29 |
| C-10 | $CH_2CH_2NH_2$ | OH | 30 |

The oxidation of the thioether (Compound B) to the sulfone (Compound C) is carded out with about two molar amounts of the oxidant. When one molar amount of oxidant is employed, the product is a sulfoxide which may then be converted to the sulfone. The sulfoxides may be employed as an intermediate in the formation the aza compounds but the sulfone is preferred. A slight excess over the two molar amount of the oxidizing agent is employed.

The reaction is carried out in an aqueous medium, preferably a mixture of acetonitrile and water. About equal amounts are preferred although a range of 1:9 to 9:1 may be employed.

In carrying out the reaction, the oxidant is added to a solution of Compound B (Seq 1D Nos. 21–30) in 1:1 acetonitrile/water and the mixture allowed to stand at ambient temperature for time sufficient to complete the reaction to obtain Compound C generally from about 30 minutes to one hour.

After completion of the reaction, the compound is recovered from the reaction mixture by diluting with water and chromatographing. Reverse phase (C18)flash column chromatography is suitable in this purification step. The preferred elating agent is 30–45 percent acetonitrile/water (0.1% TFA) in 5 percent step gradients. The appropriate fractions are lyophilized to recover the desired sulfone intermediate, Compound C (Seq ID Nos. 21–30). The intermediate tends to be labile, thus the isolation should be carried out as rapidly as possible.

Compound C may be converted to a compound having a nitrogen directly attached to the "C-5-orn". As seen in the flow diagram, reaction of Compound C with an alkali metal azide produces an azide at that position (Compound D) while reaction with an amine compound (ammonia or amine) produces an amino group at the "C-5-orn" position, (Compound I). Compound D is an important intermediate for most of the compounds of the present invention. Although Compound D has nitrogen at "C-5-orn", since it is not a product, separate sequence ID Nos. are assigned for Compound D. Sequence ID Nos. for Compound D are found in the following table.

| Compound | $R_1$ | $R_2$ | Azide SEQ ID NO. |
| --- | --- | --- | --- |
| D-1 | $CH_2CONH_2$ | $CH_3$ | 31 |
| D-2 | $CH_2CN$ | $CH_3$ | 32 |
| D-3 | $CH_2CH_2NH_2$ | $CH_3$ | 33 |
| D-4 | $CH_3$ | $CH_3$ | 34 |
| D-5 | $CH_2CONH_2$ | H | 35 |
| D-6 | $CH_2CN$ | H | 36 |
| D-7 | $CH_2CH_2NH_2$ | H | 37 |
| D-8 | $CH_2CONH_2$ | OH | 38 |
| D-9 | $CH_2CN$ | OH | 39 |
| D-10 | $CH_2CH_2NH_2$ | OH | 40 |

The azide may be obtained by adding alkali metal azide while stirring at ambient temperature to a solution of the sulfone (Compound C; Seq. ID Nos. 21–30) in an aprotic solvent for time sufficient to complete the reaction with the formation of the azide as determined by HPLC analysis. The reaction mixture then may be diluted with aqueous acid such as trifluoroacetic acid and then chromatographed to separate the desired azide (Compound D) from the reaction mixture. Reverse-phase (C 18) flash column chromatography using 10–25 percent acetonitrile/water (0.1% TFA) in 5 percent step gradients is suitable for this procedure.

The azide (Compound D) may then be reduced to a compound having a free amino group which is among the products (Compound I, Seq ID Nos. 1–10) of the present invention.

The reduction may be carded out by mixing the azide compound (Compound I) with Pd/C in a solvent such as glacial acetic acid and hydrogenating under balloon pressure for 10 to 20 hours. The product then may be recovered by first removing the catalyst by filtration and the filtrate lyophilized to obtain the amine compound (Seq ID Nos. 1–10) in which the amine is a primary amine.

The amine thus obtained may be converted into a substituted amine as subsequently described.

Compound I in which -$NR^{II}R^{III}$ is represented by -$NHCH_2CH_2NH_2$ or generically by -$NH(CH_2)_{2-4}NR^{IV}R^{V}$ may be prepared from the sulfone by a method in which a diamine $H_2N(CH_2)_{2-4}NR^{IV}R^{V}$ is caused to react with the sulfone (Compound C, Seq ID Nos. 21–30.

The reaction is carried out in an aprotic solvent such as those previously named and at ambient temperature. About tenfold molar excess of the amine compound is employed. The reaction may be carried out over one to several hours.

In carrying out the reaction, the appropriate amine is added to a solution of the sulfone in anhydrous aprotic solvent and the reaction mixture stirred at ambient temperature to obtain Compound I (Seq ID Nos. 1–10) in which the substituent at "C-5-orn" is -$NR^{II}R^{III}$. The desired compound may then be recovered by diluting with aqueous trifluoroacetic acid and then chromatographing. Reverse phase (C18) flash column chromatography eluting with 10 to 25% acetonitrile/water (0.1% TFA) in 5 percent step gradients is suitable. The appropriate fractions may be lyophilized to recover the product as a trifluoroacetate salt.

The trifluoroacetate salt may be converted by dissolving the salt in water and passing through a Bio-Rad AG2-X8(Cl-) polyprep column and recovering the product as the hydrochloride salt.

The amines, prepared as above and having a primary amino group -$NH_2$ described, may then be alkylated by conventional means to obtain a substituted amino group. Briefly, alkylation may be carried out by causing an appropriately substituted alkyl halide to react with the amine (Compound I, $NR^{II}R^{III}$=-$NH_2$; Sequence ID Nos. 1–10) in an aprotic solvent in the presence of a base to obtain the monosubstituted amine (Compound I, $NR^{II}R^{III}$=-$NHR^{II}$ wherein $R^{II}$ is $C_1$-$C_4$ alkyl, $C_3$-$C_4$ alkenyl, $(CH_2)_{2-4}OH$, and $(CH_2)_{2-4}NR^{IV}R^{V}$). The latter may be recovered from the reaction mixture by conventional procedures.

The amines, prepared as above described and having a primary amino group -$NH_2$, may be acylated by conventional means to obtain an acylated amino group. The acyl group contemplated is $CO(CH_2)_{1-4}NH_2$. Since this is a primary amino group, the amino of the acylating acid is protected such as with a benzyloxycarbonyl (CBz) group before the acylation is carried out. An activated ester such as the pentafluorophenyl ester is preferably used. The acylation may be carried out in an aprotic solvent in the presence of a base such as diisopropylethylamine at ambient temperature for from one to several hours to obtain the acylation product. The product may be recovered by diluting the reaction mixture with methanol and purifying by HPLC. The protecting group may be removed by conventional hydrogenolysis. (Compound I, -$NR^{II}R^{III}$=-$NHCO(CH_2)_{1-4}NH_2$).

The amine compounds in which the amino group at the hemiaminal position is totally substituted, i.e. when neither $R^{II}$ nor $R^{III}$ is

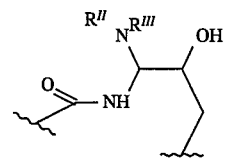

hydrogen, are preferably prepared by reacting the sulfone (Compound B, Seq ID Nos. 21–30) with an appropriately substituted amine $R^{II}R^{III}NH$. The reaction may be carded out by adding the amine to a stirred solution of the sulfone for time sufficient for reaction to take place. The product may be recovered by purifying with preparative HPLC and lyophilizing the appropriate components.

The invention also embraces acid addition salts. The compound in the normal course of isolation is obtained as an acid addition salt. Generally, it is as a trifluoroacetic acid salt. The salt thus obtained may be dissolved in water and passed through an anion exchange column beating the desired anion. The eluate containing the desired salt may be concentrated to recover the salt as a solid product.

The compounds of the present invention are active against many fungi and particularly against Candida species. The antifungal properties may be illustrated with the minimum fungicidal concentration (MFC) determination against certain Candida organisms in a microbroth dilution assay carried out in a Yeast Nitrogen Base (DIFCO) medium with 1% dextrose (YNBD).

In a representative assay, compounds are solubilized in 100% dimethyl sulfoxide (DMSO) at an initial concentration of 5 mg/ml. Once dissolved, the drag stock is brought to a concentration of 512 µg/ml by dilution in water such that the final DMSO concentration was about 10 percent. The solution is then dispensed via a multichannel pipetter into the first column of a 96-well plate (each well containing 0.075 ml of YNBD), resulting in a drug concentration of 256 µg/ml. Compounds in the first column are diluted 2-fold across the rows yielding final drug concentration ranging from 256 µg/ml to 0.12 µg/ml.

Four-hour broth cultures of organisms to be tested are adjusted using a spectrophotometer at 600 nm to equal a 0.5 McFarland Standard. This suspension is diluted 1:100 in YNBD to yield a cell concentration of 1–5×$10^4$ colony forming units (CFU)/ml. Aliquots of the suspension (0.075 ml) are inoculated into each well of the microtiter plate resulting in a final cell inoculum of 5–25×$10^3$. CFU/ml and final drug concentrations ranging from 128 µg/ml to 0.06 µg/ml. Each assay includes one row for drug-free control wells and one row for cell-free control wells.

After 24 hours of incubation, the microtiter plates are shaken gently on a shaker to resuspend the cells. The MIC-2000 inoculator is used to transfer a 1.5 microliter sample from each well of the 96-well microtiter plate to a single reservoir inoculum plate containing Sabouraud dextrose agar (SDA). The inoculated SDA plates are incubated for 24 hours at 35° C. and then read for minimum fungicidal concentration (MFC). MFC is defined as the lowest concentration of drug sharing no growth or less than 4 colonies per spot.

The in vivo effectiveness of the compounds against fungi may be seen in the following assay.

Growth from an overnight SDA culture of *Candida albicans* MY 1055 is suspended in sterile saline and the cell concentration determined by hemacytometer count and the cell suspension adjusted to $3.75 \times 10^5$ cells/ml. Then 0.2 milliliter of this suspension is administered I.V. in the tail vein of mice so that the final inoculum is $7.5 \times 10^4$ cells/mouse.

The assay then is carried out by administering aqueous solutions of Compound I at various concentrations intraperitoneally (I.P.), twice daily (b.i.d.) for four consecutive days to 18 to 20 gram female DB A/2 mice, which previously had been infected with *Candida albicans* (MY 1055) in the manner described above. Distilled water is administered I.P. to *C. albicans* challenged mice as controls. After seven days, the mice are sacrificed by carbon dioxide gas, paired kidneys are removed aseptically and placed in sterile polyethylene bags containing 5 milliliters of sterile saline. The kidneys are homogenized in the bags, serially diluted in sterile saline and aliquots spread on the surface of SDA plates. The plates are incubated at 35° C. for 48 hours and yeast colonies are enumerated for determination of colony forming units (CFU) per gram of kidneys.

A harmful and potentially fatal side reaction of a number of drugs including certain antibiotically active echinocandin compounds is red blood cell lysis. This is not seen in compounds having the present nuclei which is another advantage of the compounds of this invention. Additionally, the compounds of this invention are less toxic than certain alkyl side chain hexapeptide analogs.

The compounds of the present invention may also be also useful for inhibiting or alleviating *Pneumocystis carinii* infections in immune-compromised patients. The efficacy of the compounds of the present invention for therapeutic or anti-infection purposes may be demonstrated in studies on immunosuppressed rats.

Sprague-Dawley rats (weighing approximately 250 grams) are immunosuppressed with dexamethasone in the drinking water (2.0 mg/L) and maintained on a low protein diet for seven weeks to induce the development of Pneumocystis pneumonia from a latent infection. Before drug treatment, two rats are sacrificed to confirm the presence of *Pneumocystis carinii* pneumonia (PCP). Five rats (weighing approximately 150 grams) are injected twice daily for four days subcutaneously (sc) with Compound in 0.25 ml of vehicle (distilled water). A vehicle control is also carded out. All animals continue to receive dexamethasone in the drinking water and low protein diet during the treatment period. At the completion of the treatment, all animals are sacrificed, the lungs are removed and processed, and the extent of disease determined by microscopic analysis of stained slides. The prevention or reduction of cysts are seen in slides of the lungs of treated rats when compared with the number of cysts in the lungs of untreated controls or solvent controls.

The outstanding properties are most effectively utilized when the compound is formulated into novel pharmaceutical compositions with a pharmaceutically acceptable carrier according to the conventional pharmaceutical compounding techniques.

The novel compositions contain at least a therapeutic antifungal or antipneumocystis amount of the active compound. Generally, the composition contains at least 1% by weight of Compound I. Concentrate compositions suitable for dilutions prior to use may contain 90% or more by weight. The compositions include compositions suitable for oral, topical, parenteral (including intraperitoneal, subcutaneous, intramuscular, and intravenous), nasal, and suppository administration, or insufflation. The compositions may be prepacked by intimately mixing Compound I with the components suitable for the medium desired.

Compositions formulated for oral administration may be a liquid composition or a solid composition. For liquid preparation, the therapeutic agent may be formulated with liquid carriers such as water, glycols, oils, alcohols, and the like, and for solid preparations such as capsules and tablets, with solid carriers such as starches, sugars, kaolin, ethyl cellulose, calcium and sodium carbonate, calcium phosphate, kaolin, talc, lactose, generally with lubricant such as calcium stearate, together with binders disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Compositions in unit dosage form constitute an aspect of the present invention.

Compositions may be formulated for injection and may take such forms as suspensions, solutions or emulsions in oily or aqueous vehicles such as 0.85 percent sodium chloride or 5 percent dextrose in water and may contain formulating agents such as suspending, stabilizing and/or dispersing agents. Buffering agents as well as additives such as saline or glucose may be added to make the solutions isotonic. The compound may also be solubilized in alcohol/propylene glycol or polyethylene glycol for drip intravenous administration. These compositions also may be presented in unit dosage form in ampoules or in multidose containers, preferable with added preservative. Alternatively, the active ingredients may be in powder form for reconstituting with a suitable vehicle prior to administration.

The term "unit dosage form" as used in the specification and claims refers to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

When the compound is for antifungal use, any method of administration may be employed. For treating mycotic infections, oral or intravenous administration is usually employed.

When the compound is to be employed for control of Pneumocystis infections it is desirable to directly treat lung and bronchi. For this reason inhalation methods are preferred. For administration by inhalation, the compounds of the present inventions are conveniently delivered in the form of an aerosol spray presentation from pressurized packs or nebulisers. The preferred delivery system for inhalation is a metered dose inhalation (MDI) aerosol, which may be formulated as a suspension or solution of Compound I in suitable propellants, such as fluorocarbons or hydrocarbons.

Although the compounds of the present invention may be employed as tablets, capsules, topical compositions, insufflation powders, suppositories and the like, the solubility of the compounds of the present invention in water and aqueous media render them adaptable for use in injectible formulations and also in liquid compositions suitable for aerosol sprays.

The following examples illustrate the invention but are not to be construed as limiting.

EXAMPLE 1

HPLC (ZORBAX C18, 40% acetonitrile/water/0.1% TFA, 210 nm) to obtain the desired compound as a trifluroacetate salt with a molecular weight of 1342.

Part B. Oxidation to Sulfone (SEQ ID No. 25)

The mixture of thioethers obtained as described above (0.716 mmol) is dissolved in 30 mL of 1:1 acetonitrile/water and "OXONE" (1.06 mmol equivalents of potassium hydrogen persulfate) is added. After about an hour, the solution is diluted with an equal volume of water and rapidly chromatographed using reverse phase C18 flash chromatography eluting with 35–45% acetonitrile/water containing 0.1% TFA in 2% step gradients. The product containing fractions as determined by analytical HPLC ("ZORBAX" C18, 35% acetonitrile/water/0.1% TFA, 210 nm) are lyophilized to give the desired product with a molecular weight of 1374.4.

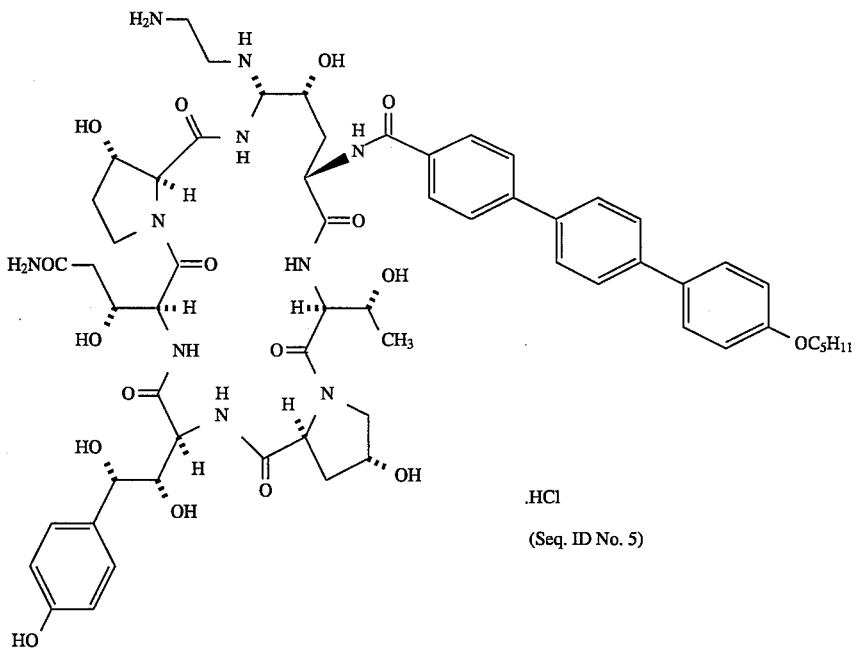

.HCl (Seq. ID No. 5)

Part A. Preparation of Aminoethylthioether Intermediate (SEQ ID NO. 25)

A solution of the lipopeptide ($R_1$=CH$_2$CONH$_2$, $R_2$=H, $R'$=4"-(n-pentyloxy)-[1,1':4',4"-terphenyl]-4-yl) (1.00 mmol), 2-aminoethanethiol hydrochloride (100 mmol) and (1S)-(+)-10-camphorsulfonic acid (1.00 mmol) in 80 mL of anhydrous N,N-dimethylformamide is stirred at 25° C. for 2–6 days or a period sufficient effect dissapearance of the starting material. The reaction is diluted with 80 milliliters of water and flash chromatographed on "LICHROPREP" (E. Merck) RP 18 (40–63 μm, 30 grams) packed in 10 percent acetonitrile/water. The column is eluted with 10 to 40 percent acetonitrile/water collecting several fractions at each gradient step. The appropriate fractions, as determined by analytical HPLC (Zorbax Rx C18, 40% acetonitrile/water/ 0.1% trifluoroacetic acid, 210 nm) are concentrated and lyophilized. The residue is further purified by preparative

Part C. Displacement of Sulfone with Ethylenediamine

The sulfone mixture (0.94 mmol), obtained as described in Part B above, is dissolved in 20 mL of anhydrous DMF and ethylenediamine (9.40 mmol) is added. The mixture is stirred for about 1–12 hours or until analytical HPLC analysis (RP-18, 30% acetonitrile/water/0.1% TFA, 210 nm) shows complete disappearance of the starting sulfone isomers. The mixture is separated by reverse phase (C18) flash column chromatography eluting with 10–30% acetonitrile/ water/0.1% TFA in 5% step gradients. The appropriate fractions are pooled, frozen and lyophilized to give the desired product with the α-C-5 orn configuration and its β-C-5 orn epimer. The trifluoroacetate salt thus obtained is dissolved in a small volume of deionized water and passed through a Bio-Rad AG2-X8 (Cl⁻) polyprep column washing with additional water. The product-containing eluate is lyophilized to give the desired product as the hydrochloride salt with a molecular weight of 1247.81.

EXAMPLE 2

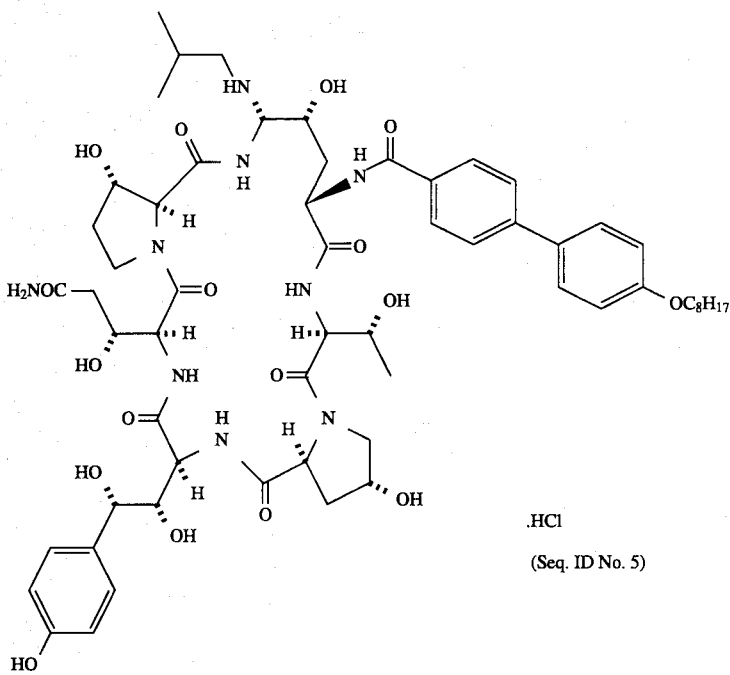

.HCl (Seq. ID No. 5)

Part A. Preparation of Aminoethylthioether Intermediate (SEQ ID No. 25

Starting with the lipopeptide where ($R_1$=$CH_2CONH_2$, $R_2$=H, $R'$=4'-(n-octyloxy)-[p-biphenyl]-4-yl), (1.00 mmol), 2-aminoethanethiol hydrochloride (100 mmol) and (1S)-(+)-10-camphorsulfonic acid (1.00 mmol) in 80 mL of anhydrous N,N-dimethylformamide is stirred at 25° C. for 2–6 days or a period sufficient to effect disappearance of the starting material. The reaction is diluted with 80 milliliters of water and flash chromatographed on "LICHROPREP" (E. Merck) RP 18 (40–63 μm, 30 grams) packed in 10 percent acetonitrile/water. The column is eluted with 10 to 40 percent acetonitrile/water collecting several fractions at each gradient step. The appropriate fractions, as determined by analytical HPLC (Zorbax Rx C18, 40% acetonitrile/water/0.1% trifluoroacetic acid, 210 nm) are concentrated and lyophilized. The residue is further purified by preparative HPLC ("ZORBAX" C18, 40% acetonitrile/water/0.1% TFA, 210 nm) to obtain the desired compound as a trifluoroacetate salt with a molecular weight of 1308.40.

Part B. Oxidation to Sulfone (SEQ ID .No. 25)

The mixture of thioethers obtained as described in Part A above (0.716 mmol) is dissolved in 30 mL of 1:1 acetonitrile/water and "OXONE" (1.06 mmol equivalents of potassium hydrogen persulfate) is added. After about an hour, the solution is diluted with an equal volume of water and rapidly chromatographed using reverse phase C18 flash chromatography eluting with 35–45% acetonitrile/water containing 0.1% TFA in 2% step gradients. The product containing fractions as determined by analytical HPLC ("ZORBAX" C18, 35% acetonitrile/water/0.1% TFA, 210 nm) are lyophilized to give the desired product with a molecular weight of 1340.40.

Part C. Displacement of Sulfone with Isobutylamine

The sulfone mixture (0.94 mmol), obtained as described in Part B above, is dissolved in 20 mL of anhydrous DMF and isobutylamine (9.40 mmol) is added. The mixture is stirred for about 1–12 hours or until analytical HPLC analysis (RP-18, 30% acetonitrile/water/0.1% TFA, 210 nm) shows complete disappearance of the starting sulfone isomers. The mixture is separated by reverse phase (C18) flash column chromatography eluting with 10–30% acetonitrile/water/0.1% TFA in 5% step gradients. The appropriate fractions are pooled, frozen and lyophilized to give the desired product with the α-C-5 orn configuration and its β-C-5 orn epimer. The trifluoroacetate salt thus obtained is dissolved in a small volume of deionized water and passed throu a Bio-Rad AG2-X8 (Cl⁻) polyprep column washing with additional water. The product-containing eluate is lyophilized to give the desired product as the hydrochloride salt with a molecular weight of 1226.83.

EXAMPLES 3–5
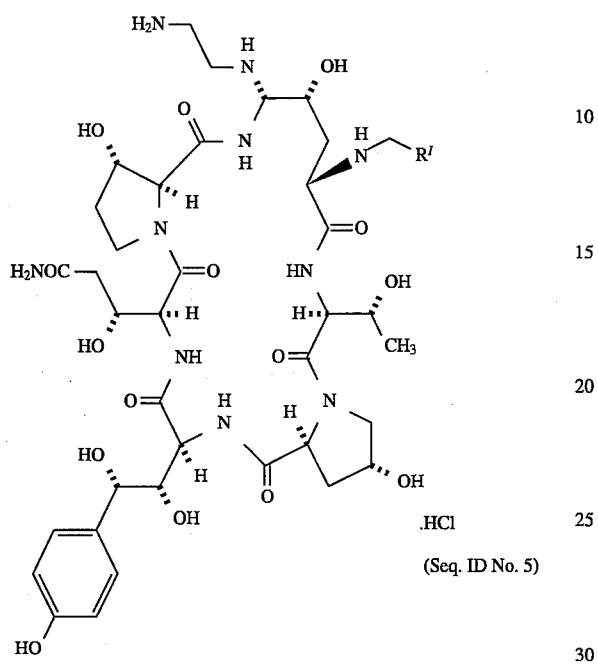
(Seq. ID No. 5)
In a completely analogous fashion to Example 1, but starting with the appropriate side chain variant of the lipopeptide, the following compounds indicated in Table 1 may be prepared:
TABLE 1
| $R^I$ | Molecular Weight of Product |
|---|---|
| 4'-octyloxy-biphenyl (—C6H4—C6H4—OC8H17) | 1213.79 |
| biphenyl-O-CH2CH2-N(piperazine)-NC11H23 | 1404.51 |
| biphenyl-O-CH2CH2-N(piperidine-4-CH2-cyclohexyl) | 1345.40 |
EXAMPLE 6

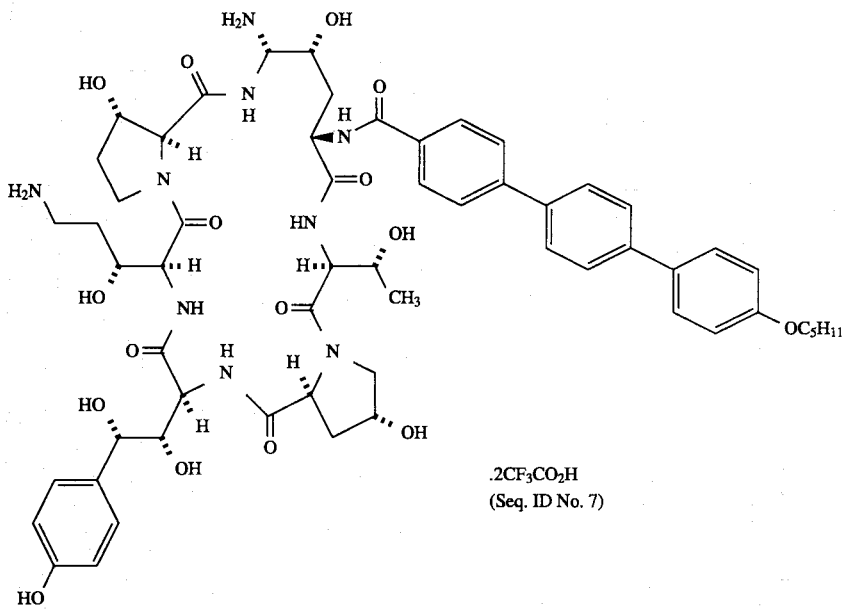

.2CF₃CO₂H
(Seq. ID No. 7)

Part A. Preparation of Intermediate Nitrile Compound (SEQ ID No. 6)

A solution of the lipopeptide ($R_1$=CH$_2$CONH$_2$, $R_2$=H, $R^I$=4"-(n-pentyloxy)-[1,1':4',4"-terphenyl]-4-yl) (1.0 eq) is prepared in sieve-dried DMF and approximately 3 molar equivalents of cyanuric chloride are added in one portion. After 5–6 minutes, the reaction is quenched with 10 molar equivalents of aqueous sodium acetate. The reaction mixture is diluted with 50% aqueous acetonitrile, purified by preparative HPLC (C18 "ZORBAX" DuPont, step gradient starting at 70/30: H$_2$O/CH$_3$CN/0.1% TFA) and the appropriate fractions lyophilized to obtain the desired product as a solid (MW=1151.25).

Part B. Preparation of the Amine Compound (SEQ ID No. 7)

To a solution of the nitrile compound from Part A above (1.0 eq) in methanol is added cobalt (II) chloride (4.0 eq). Next, NaBH$_4$ (20 eq) is added cautiously and in several portions. The black reaction is stirred for several hours at which time sufficient 2N hydrochloric acid is added to effect dissolution of the precipitate. The resulting solution is diluted with water and purified by preparative HPLC (C18 "ZORBAX", step gradient starting at 70/30: H$_2$O/CH$_3$CN/ 0.1% TFA). The appropriate fractions are combined and lyophilized to obtain the desired water soluble product (MW=1269.32).

Part C. Preparation Of Aminoethylthioether Intermediate (SEQ ID No. 27)

A solution of the 3-hydroxyornithine intermediate from Part B above (0.47 mmol), 2-aminoethanethiol hydrochloride (47 mmol) and (1S)-(+)-10-camphorsulfonic acid (0.47 mmol) in 40 milliliters of anhydrous N,N-dimethylformamide is stirred at 25° C. for 2–6 days or a period sufficient effect dissapearance of the starting material. The reaction is diluted with 40 milliliters of water and flash chromatographed on "LICHROPREP" (E. Merck) RP 18 (40–63 μm, 15 grams) packed in 10 percent acetonitrile/water. The column is eluted with 10 to 40 percent acetonitrile/water collecting several fractions at each gradient step. The appropriate fractions, as determined by analytical HPLC (Zorbax Rx C18, 40% acetonitrile/water/0.1% trifluoroacetic acid, 210 nm) are concentrated and lyophilized. The residue is further purified by preparative HPLC (ZORBAX C18, 40% acetonitrile/water/0.1%TFA, 210 nm) to obtain the desired compound as a trifluroacetate salt with a molecular weight of 1442.

Part D. Oxidation to Sulfone (SEQ ID No. 27).

The mixture of thioethers obtained as described above (0.358 mmol) is dissolved in 15 mL of 1:1 acetonitrile/water and "OXONE" (1.06 mmol equivalents of potassium hydrogen persulfate) is added. After about an hour, the solution is diluted with an equal volume of water and rapidly chromatographed using reverse phase C18 flash chromatography eluting with 35–45% acetonitrile/water containing 0.1% TFA in 2% step gradients. The product containing fractions are lyophilized to give the product with a molecular weight of 1474.

Part E. Displacement Of Sulfones with Azide (SEQ ID No. 37)

The mixture of sulfones (0.257 mmol), prepared as described above, is dissolved in 10 mL of anhydrous DMF. Lithium azide (0.257 mmol) is added as a solid and the mixture is stirred for about a 4–24 hours. The mixture is purified by reverse phase C18 flash chromatography eluting with 30–65% acetonitrile/water in 5% step gradients. The appropriate fractions, as determined by reverse phase HPLC (RP-18, 40% acetonitrile/water/0.1% TFA, 210 nm) are pooled, frozen and lyophilized to give the crude product. Further purification by preparative reverse phase HPLC (C18, 40–45% acetonitrile/water/0.1% TFA, 210 nm) yields the desired purified compound as a trifluoroacetate salt with a molecular weight of 1294.

Part F. Reduction of Azide to Amine (SEQ ID No. 7)

A mixture of the azido compound (0.126 mmol) (obtained as described above) and 10% Pd on charcoal (100–150 mg) is suspended in glacial acetic acid (10 mL). The reaction vessel is flushed first with nitrogen then with hydrogen. One atmosphere pressure of hydrogen gas is maintained for a period of time sufficient to give complete reduction to the amine product, typically 2 to 24 h. The catalyst is removed by filtration and the filtrate is lyophilized to obtain the crude amine. Further purification may be accomplished by preparative reverse phase chromatography (C18, 35–41% acetonitrile/water/0.1% TFA in 3% step gradients, 210 nm). The product-containing fractions are lyophilized to give the purified compound with a molecular weight of 1382.

Part B. Reduction of the Azido Group to Amine (SEQ ID No. 7)

The azido compound prepared in Part A above (0.05mmol) is dissolved in 1 mL of 10% aqueous tetrahydrofuran. Triphenylphosphine (0.10 mmol) is added and the mixture is stirred for 24 hours or until no starting material remains as determined by analytical HPLC ("ZORBAX" C18, 50% acetonitrile/water/0.1% TFA, 210 nm). The volatiles are removed by rotary evaporation under reduced pressure and the residue dissolved in a minimal amount of 40% aqueous methanol and purified by preparative HPLC ("ZORBAX" C18, 70% water/acetonitrile/0.1% TFA to 50% water/acetonitrile/0.1% TFA, 3 step gradient, 210 nm). The product-containing fractions are pooled, frozen and lyophilized to give the desired amino compound as a trifluoroacetate salt with a molecular weight of 1402.46.

EXAMPLE 7

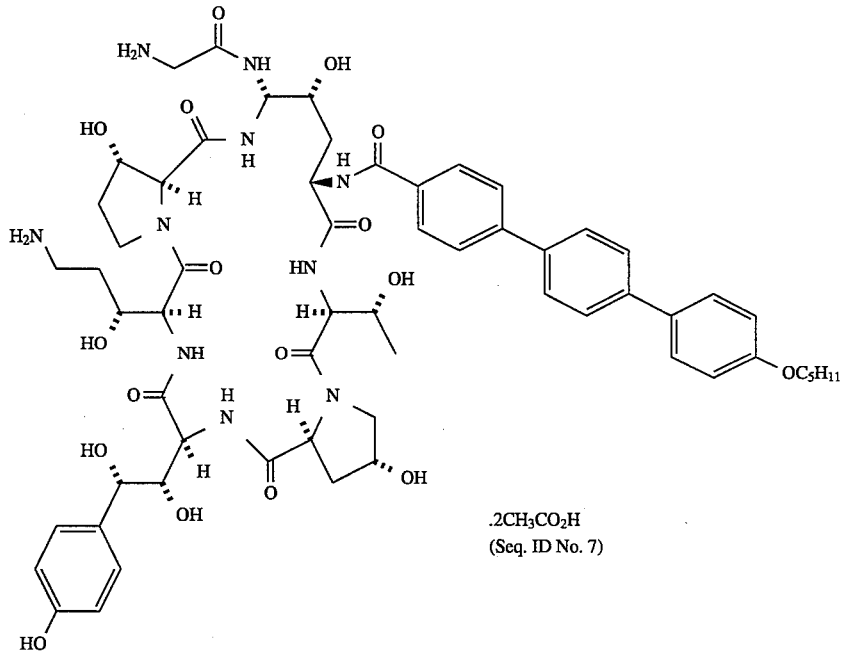

.2CH₃CO₂H
(Seq. ID No. 7)

Part A. Protection of 3-Hydroxyornithine Residue with Benzyloxycarbonyl Group (SEQ ID No. 7)

The azido compound (0.10 mmol), obtained as in Part E of Example 6, is dissolved in 1 mL of anhydrous N,N-dimethylformamide under a nitrogen atmosphere. p-Nitrophenyl benzylcarbonate (0.15 mmol) and triethylamine (0.15 mmol) are added and the reaction is stirred at room temperature for 6–12 hours or until analysis by analytical HPLC ("ZORBAX" C18, 50% acetonitrile/water/0.1% TFA, 210 and 277 nm) indicates the reaction is complete. The mixture is diluted with 1 mL of methanol and purified by preparative HPLC ("ZORBAX" C18, 70% water/acetonitrile/0.1% TFA to 50% water/acetonitrile/0.1% TFA, 2 step gradient, 210 nm) to give the desired N-protected compound with a molecular weight of 1314.43.

Part C. Acylation with Protected Glycine (SEQ ID No. 7)

The amino compound (0.10 mmol), obtained as described in Part B above, is dissolved in 1 mL of anhydrous N,N-dimethylformamide under a nitrogen atmosphere. Diisopropylethylamine (0.11 mmol) and N-Carbobenzyloxyglycine pentafluorophenyl ester (0.15 mmol) are added and the reaction is stirred at room temperature for 1–12 hours or until analysis by analytical HPLC ("ZORBAX" C18, 50% acetonitrile/water/0.1% TFA, 210 and 277 nm) indicates the reaction is complete. The mixture is diluted with 1 mL of methanol and purified by preparative HPLC ("ZORBAX" C18, 70% water/acetonitrile/0.1% TFA to 35% water/acetonitrile/0.1% TFA, 2 step gradient, 210 nm) to give the desired glycylated compound with a molecular weight of 1479.62.

Part D. Hydrogenolysis Of Carbobenzyloxy-Protected Glycine Compound (SEQ ID No. 7)

The pure carbobenzyloxy-protected compound (0.075 mmol) obtained as in Part C above, is dissolved in a mixture of 3 mL of methanol, 1 mL of water and 0.2 mL of glacial acetic acid. Next, 50 mg of 10% palladium on charcoal is added and the reaction vessel is flushed first with nitrogen, then hydrogen. The reaction is stirred rapidly under 1 atmosphere of hydrogen for several hours. The catalyst is removed by filtration and the volatiles are removed by rotary evaporation under reduced pressure. The residue is dissolved in 2 mL of water, frozen and lyophilized to give the desired deprotected amine product as an acetate salt. The product has a molecular weight of 1331.

EXAMPLE 8

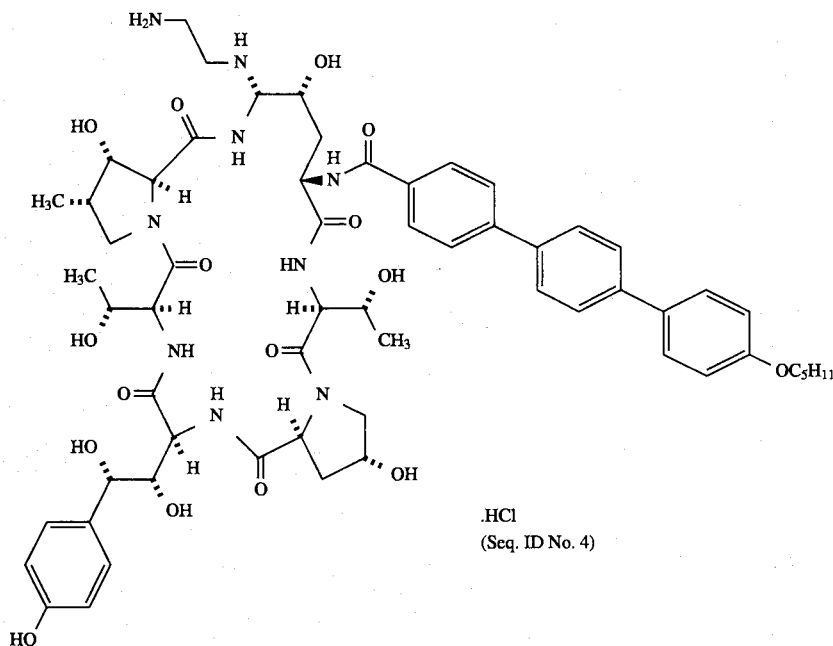

.HCl
(Seq. ID No. 4)

Part A. Preparation of Aminoethylthioether Intermediate (SEQ ID No. 24)

A solution of the lipopeptide ($R_1$=$CH_3$, $R_2$=$CH_3$, $R'$= 4"-(n-pentyloxy)-[1,1':4',4"-terphenyl]-4-yl) intermediate (0.47 mmol), 2-aminoethanethiol hydrochloride (47 mmol) and (1S)-(+)-10-camphorsulfonic acid 0.47 mmol in 40 milliliters of anhydrous N,N-dimethylformamide is stirred at 25° C. for 2–6 days or a period sufficient to effect disappearance of the starting material. The reaction is diluted with 40 milliliters of water and flash chromatographed on "LICHROPREP" (E. Merck) RP 18 (40–63 µm, 15 grams)packed in 10 percent acetonitrile/water. The column is eluted with 10 to 40 percent acetonitrile/water collecting two 120 milliliter fractions at each gradient step. The appropriate fractions, as determined by analytical HPLC (Zorbax Rx C18, 40% acetonitrile/water/0.1% trifluoroacetic acid, 210 nm) are concentrated and lyophilized. The residue is further purified by preparative HPLC ("ZORBAX" C18, 40% acetonitrile/water/0.1% TFA, 210 nm) to obtain the desired isomeric mixture of compounds as the trifluroacetate salt with a molecular weight of 1313.

Part B. Oxidation to Sulfone. (SEQ ID No. 24)

The mixture of thioethers obtained as described above in Part A (0.358 mmol) is dissolved in 15 mL of 1:1 acetonitrile/water and "OXONE" (1.06 mmol equivalents of potassium hydrogen persulfate) is added. After about an hour, the solution is diluted with an equal volume of water and rapidly chromatographed using reverse phase C18 flash chromatography eluting with 35–45% acetonitrile/water containing 0.1% TFA in 2% step gradients. The product containing fractions as determined by analytical HPLC ("ZORBAX" C18, 45% acetonitrile/water/0.1% TFA, 210 nm) are lyophilized to give the product with a molecular weight of 1345.

Part C. Displacement of Sulfone with Ethylenediamine (SEQ ID No.4)

The sulfone mixture (0.15 mmol), obtained as described in Part B above, is dissolved in 3.0 mL of anhydrous DMF and ethylenediamine (1.50 mmol) is added. The mixture is stirred for about 1–12 hours or until analytical HPLC analysis (RP-18, 30% acetonitrile/water/0.1% TFA, 210 nm) shows complete disappearance of the starting sulfone. The mixture is separated by reverse phase (C18) flash column chromatography eluting with 10–30% acetonitrile/water/ 0.1% TFA in 5% step gradients. The appropriate fractions are pooled, frozen and lyophilized to give the desired product with the α-C-5 orn configuration and its β-C-5 orn epimer. The trifluoroacetate salt thus obtained is dissolved in a small volume of deionized water and passed throu a Bio-Rad AG2-X8 (Cl⁻) polyprep column washing with additional water. The product-containing eluate as determined by analytical HPLC ("ZORBAX" RX-C18, 30% acetonitrile/water/0.1% TFA, 210 nm) is lyophilized to give the desired product as the hydrochloride salt with a molecular weight of 1218.81.

EXAMPLE 9

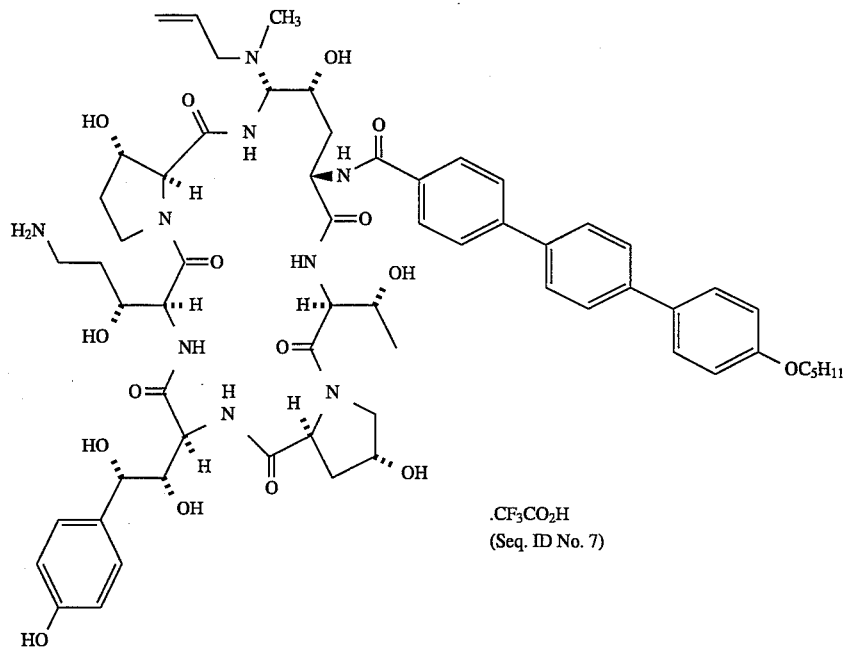

.CF$_3$CO$_2$H
(Seq. ID No. 7)

The sulfone mixture (0.15 mmol), obtained as described in Part D of Example 6, is dissolved in 3.0 mL of anhydrous DMF and N-methyl-N-allylamine (1.50 mmol) is added. The mixture is stirred for about 1–12 hours or until analytical HPLC analysis (RP-18, 30% acetonitrile/water/0.1% TFA, 210 nm) shows complete disappearance of the starting sulfone. The mixture is separated by reverse phase (C18) flash column chromatography eluting with 10–40% acetonitrile/water/0.1% TFA in 5% step gradients. The appropriate fractions as determined by analytical HPLC ("ZORBAX" RX-C18, 35% acetonitrile/water/0.1% TFA, 210 nm) are pooled, frozen and lyophilized to give the desired product with the α-C-5 orn configuration and its β-C-5 orn epimer. The trifluoroacetate salt thus obtained has a molecular weight of 1435.43.

EXAMPLE 10

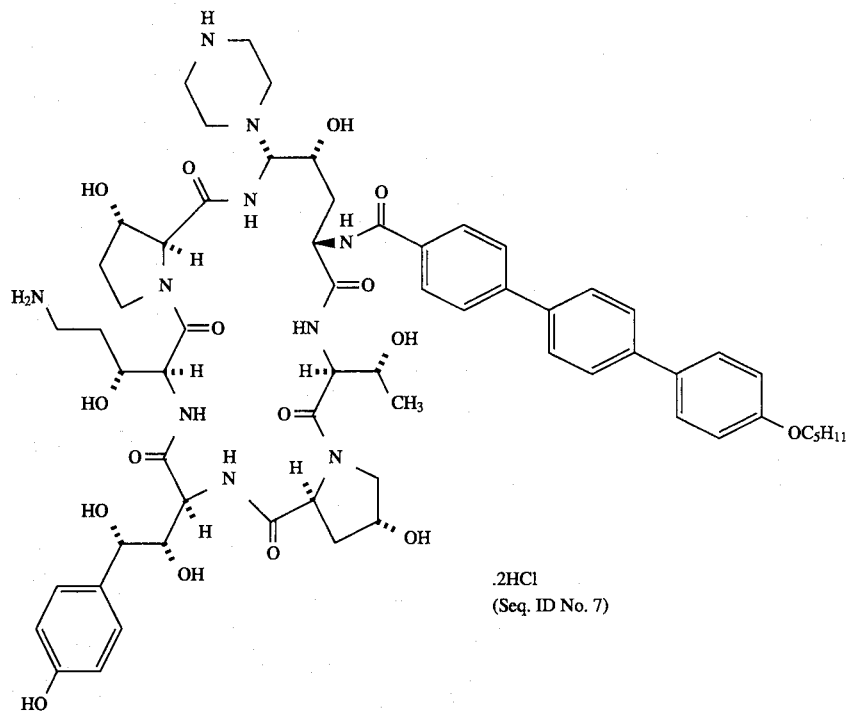

.2HCl
(Seq. ID No. 7)

The sulfone mixture (0.3 mmol), obtained as described in Part D of Example 6, is dissolved in 6.0 mL of anhydrous DMF and piperazine (3.0 mmol) is added. The mixture is stirred for about 1–12 hours or until analytical HPLC analysis (RP-18, 30% acetonitrile/water/0.1% TFA, 210 nm) shows Complete disappearance of the starting sulfone. The mixture is separated by reverse phase (C18) flash column chromatography eluting with 10–30% acetonitrile/water/ 0.1% TFA in 5% step gradients. The appropriate fractions as determined by analytical HPLC ("ZORBAX" RX-C18, 30% acetonitrile/water/0.1% TFA, 210 nm) am pooled, frozen and lyophilized to give the desired product with the α-C-5 orn configuration and its β-C-5 orn epimer. The trifluoroacetate salt thus obtained is dissolved in a small volume of deionized water and passed throu a Bio-Rad AG2-X8 (Cl⁻) polyprep column washing with additional water. The product-containing eluate is lyophilized to give the desired product as the dihydrochloride salt with a molecular weight of 1296.32.

EXAMPLE 11

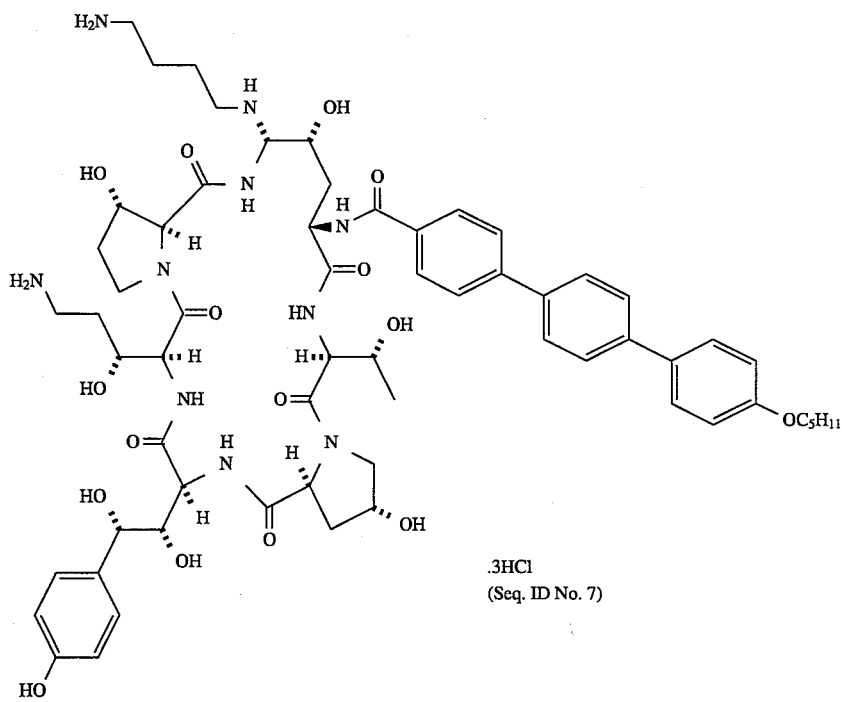

.3HCl
(Seq. ID No. 7)

The sulfone mixture (0.3 mmol), obtained as described in Part D of Example 6, is dissolved in 6.0 mL of anhydrous DMF and 1,4-diaminobutane (3.0 mmol) is added. The mixture is stirred for about 1–12 hours or until analytical HPLC analysis (RP-18, 30% acetonitrile/water/0.1% TFA, 210 nm) shows complete disappearance of the starting sulfone. The mixture is separated by reverse phase (C18) flash column chromatography eluting with 10–30% acetonitrile/water/0.1% TFA in 5% step gradients. The appropriate fractions as determined by analytical HPLC ("ZORBAX" RX-C18, 30% acetonitrile/water/0.1% TFA, 210 nm) am pooled, frozen and lyophilized to give the desired product with the α-C-5 orn configuration and its β-C-5 orn epimer. The trifluoroacetate salt thus obtained is dissolved in a small volume of deionized water and passed throu a Bio-Rad AG2-X8 (Cl⁻) polyprep column washing with additional water. The product-containing eluate is lyophilized to give the desired product as the trihydrochloride salt with a molecular weight of 1334.80.

EXAMPLE 12

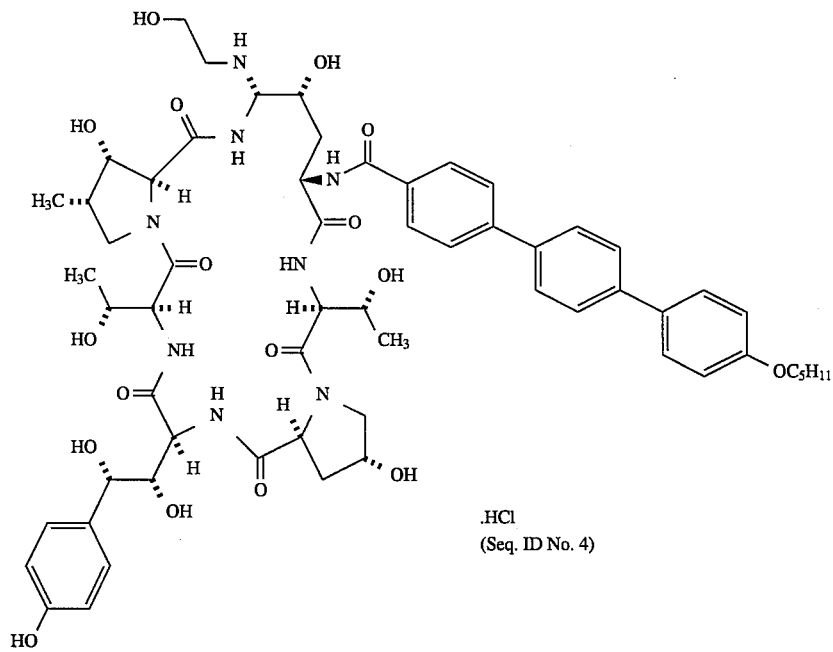

.HCl
(Seq. ID No. 4)

The sulfone mixture (0.3 mmol), obtained as described in Part B of Example 8, is dissolved in 6.0 mL of anhydrous DMF and ethanolamine (3.0 mmol) is added. The mixture is stirred for about 1–12 hours or until analytical HPLC analysis (RP-18, 30% acetonitrile/water/0.1% TFA, 210 nm) shows complete disappearance of the starting sulfone. The mixture is separated by reverse phase (C18) flash column chromatography eluting with 10–30% acetonitrile/water/ 0.1% TFA in 5% step gradients. The appropriate fractions as determined by analytical HPLC ("ZORBAX" RX-C18, 30% acetonitrile/water/0.1% TFA, 210 nm) are pooled, frozen and lyophilized to give the desired product with the α-C-5 orn configuration and its β-C-5 orn epimer. The trifluoroacetate salt thus obtained is dissolved in a small volume of deionized water and passed throu a Bio-Rad AG2-X8 (Cl⁻) polyprep column washing with additional water. The product-containing eluate is lyophilized to give the desired product as the hydrochloride salt with a molecular weight of 1219.80.

EXAMPLE 13

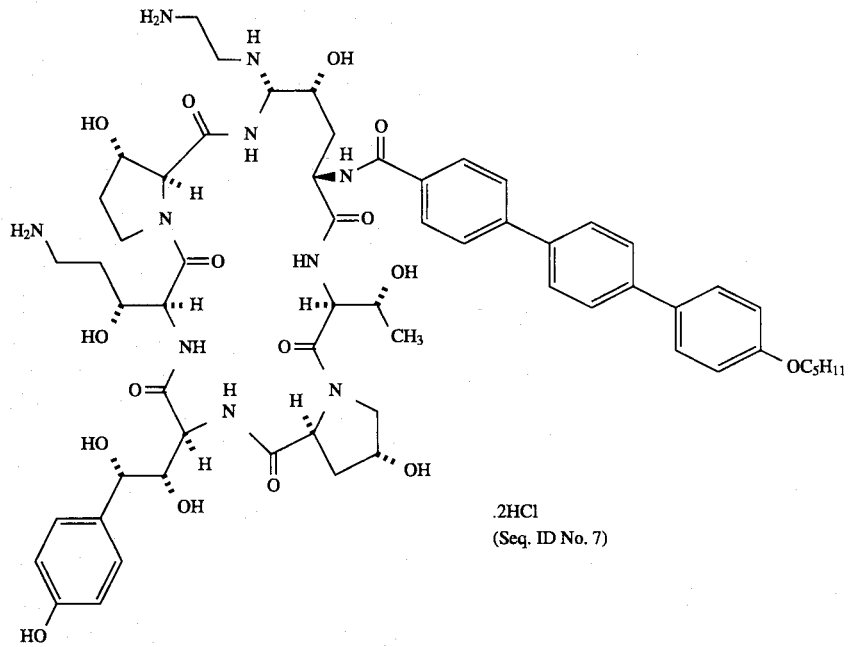

.2HCl
(Seq. ID No. 7)

The sulfone mixture (0.3 mmol), obtained as described in Part D of Example 6, is dissolved in 6.0 mL of anhydrous DMF and ethylenediamine (3.0 mmol) is added. The mixture is stirred for about 1–12 hours or until analytical HPLC analysis (RP-18, 30% acetonitrile/water/0.1% TFA, 210 nm) shows complete disappearance of the starting sulfone. The mixture is separated by reverse phase (C18) flash column chromatography eluting with 10–30% s acetonitrile/water/ 0.1% TFA in 5% step gradients. The appropriate fractions as determined by analytical HPLC ("ZORBAX" RX-C18, 30% acetonitrile/water/0.1% TFA, 210 nm) are pooled, frozen and lyophilized to give the desired product with the α-C-5 orn configuration and its β-C-5 orn epimer. The trifluoroacetate salt thus obtained is dissolved in a small volume of deionized water and passed throu a Bio-Rad AG2-X8 (Cl⁻) polyprep column washing with additional water. The product-containing eluate is lyophilized to give the desired product as the dihydrochloride salt with a molecular weight of 1270.29.

The following examples illustrate representative formulations employing the compounds of this invention.

COMPOSITION EXAMPLE A 1000 compressed tablets each containing 500 mg of the compound of Example 13 are prepared from the following formulation:

| Compound | Grams |
| --- | --- |
| Compound of Example 13 | 500 |
| Starch | 750 |
| Dibasic calcium phosphate, hydrous | 5000 |
| Calcium stearate | 2.5 |

The finely powdered ingredients are mixed well and granulated with 10 percent starch paste. The granulation is dried and compressed into tablets.

EXAMPLE B 1000 hard gelatin capsules, each containing 500 mg of the same compound are prepared from the following formulation:

| Compound | Grams |
| --- | --- |
| Compound of Example 13 | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE C

An aerosol composition may be prepared having the following formulation:

|  | Per Canister |
| --- | --- |
| Compound of Example 13 | 24 mg |
| Lecithin NF Liquid Concd. | 1.2 mg |
| Trichlorofluoromethane, NF | 4.026 g |
| Dichlorodifluoromethane, NF | 12.15 g |

EXAMPLE D 250 milliliters of an injectible solution may be prepared by conventional procedures having the following formulation:

| Dextrose | 12.5 g |
| --- | --- |
| Water | 250 ml |
| Compound of Example 13 | 400 mg |

The ingredients are blended and thereafter sterilized for use.

PREPARATION OF STARTING MATERIALS:

A-5 when $R^I$ is DMTD may be produced by cultivating *Zalerion arboricola* ATCC 206868 in nutrient medium with mannitol as the primary source of carbon as described in U.S. Pat. No. 5,021, 341 issued Jun. 4, 1991.

A-1 when $R^I$ is DMTD may be produced by cultivating *Zalerion arboricola* ATCC 20868 in nutrient medium as described in U.S. Pat. No. 4,931,352 issued Jun. 5, 1990.

A-4 when $R^I$ is linoleyl may be produced by cultivating *Aspergillus nidulans* NRRL 11440 in nutrient medium as described in U.S. Pat. No. 4,288,549 issued Sep. 8, 1981.

A-8 may be produced by cultivation of *Zalerion arboricola* ATCC 20958 in nutrient medium as described in U.S. Pat. No. 5,306,708 issued Apr. 26, 1994.

Compounds in which $R_1$ is $CH_2CN$ such as A-2, A-6 and A-9 may be produced by the reaction of a compound having a carboxamide group in the corresponding position with excess cyanuric chloride in an aprotic solvent. Molecular sieves may be employed in this reaction. After completion of the reaction, the sieves, if employed, are removed, and the filtrate concentrated to obtain the nitrile compound as more fully described in copending application, Ser No. 936,434, Sep. 3, 1992, U.S. Pat. No. 5,348,940, issued Sep. 20, 1994.

Compounds in which $R_1$ is $CH_2CH_2NH_2$ such as A-3, A-7 and A-10 may be produced by either a chemical or catalytic reduction of the nitrile. It is conveniently carried out employing large molar excess of sodium borohydride with cobaltous chloride as more fully described in copending application Ser. No. 936,558 filed Sep. 3, 1992.

Starting materials in which $R^I$ is a different group from that of the natural product may be obtained by deacylating the lipophilic group of the natural product by subjecting the natural product in a nutrient medium to a deacylating enzyme until substantial deacylation occurs, said enzyme having first been obtained by cultivating a microorganism of the family Pseudomondaceae or Actinoplanaceae, as described in Experentia 34, 1670 (1978) or U.S. Pat. No. 4,293,482, recovering the deacylated cyclopeptide, and thereafter acylating the deacylated cyclopepetide by mixing together with an appropriate active ester $R^ICOX$ to obtain Compound A with the desired acyl group.

The active esters $R^ICOX$ may be prepared by methods known to the skilled chemist as illustrated in the following examples. Although any active ester is appropriate, the compounds are illustrated with pentafluorophenyl esters.

Preparation of Alkoxyterphenyl Side Chains

The terphenylcarboxylic acid esters may be prepared through the following sequence of reactions, illustrated with a specific example as follows:

A. Preparation of pentyloxy-substituted-terphenyl-carboxylic acid

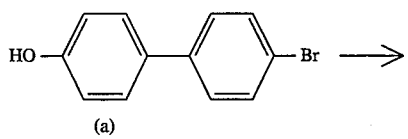
(a)

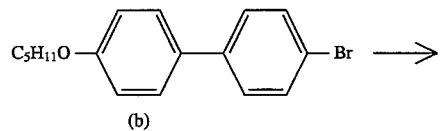
(b)

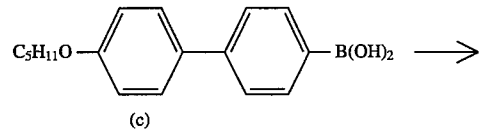
(c)

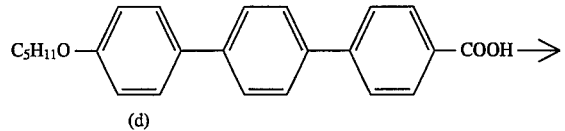
(d)

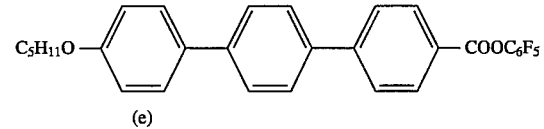
(e)

Part A: 4-(4-n-Pentyloxyphenyl) bromobenzene

To a stirred solution of 25.5 g of 4-(4-bromophenyl)phenol (Compound (a)) in 400 mL of dimethylsulfoxide was added 40.9 mL of 2.5 N NaOH, followed by 12.7 mL of n-pentyl bromide, and the resulting mixture heated at 70° C. for 18 hours to obtain in the mixture, compound (b). The mixture was partitioned between 1000 mL of ethyl acetate and 500 mL water and from the organic phase after washing with water and brine, and drying was obtained 30.9 grams of Compound (b) as a whim solid.

$^1$H NMR (400 MHz, DMSO-$d_6$) δ0.93 (t, J=7.2 Hz, 3H), 1.41 (m, 4H), 1.79 (m, 2H), 3.97 (t, J=6.6 Hz, 2H), 6.94 (d, J=8.8 Hz, 2H), 7.39 (d, J=8.6 Hz, 2H), 7.45 (d, J=8.8 Hz, 2H), 7.51 (d, J=8.6 Hz, 2H).

Part B: 4-(4-n-Pentyloxyphenyl)phenylboronic acid

To a stirred suspension of 1.0 grams of Compound (b) in 20 mL anhydrous tetrahydrofuran at −78° C. under a nitrogen atmosphere was added 1.32 mL of 2.5M n-butyl lithium in hexanes. After 15 minutes 0.760 mL of tri-isopropyl borate was added and the stirring continued at −78° C. for 15 minutes and then at 25° C. for 40 minutes. The mixture was acidified and partitioned between ether and water to obtain the boronic acid compound (c) in the reaction mixture. The compound was recovered by washing with water and brine and drying to obtain 750 mg of 4-(4-n-pentyloxyphenyl) phenylboronic acid as whim solid with the following $^1$H NMR.

$^1$H NMR (400 MHz, DMSO-$d_6$) δ0.89 (t, J=7.2 Hz, 3H), 1.38 (m, 4H), 1.72 (m, 2H), 3.99 (t, J=6.5 Hz, 2H), 6.99 (d, J=8.8 Hz, 2H), 7.57 (d, J=8.2 Hz, 2H), 7.60 (d, J=8.8 Hz, 2H), 7.83 (d, J=8.2 Hz, 2H).

Part C: Pentafluorophenyl 4"-(n-pentyloxy)-[1,1':4',1"-terphenyl]-4-carboxylate

To a stirred mixture of 1.0 g of the boronic acid and 0.0874 mL of 4-iodobenzoic acid in 11 mL ethanol and 30 mL toluene was added 5.3 mL of a 2M aqueous solution of sodium carbonate followed by 204 mg tetrakis(triphenylphosphine)palladium and the reaction mixture heated under reflux (100° C.) for 18 hours. Thereafter, the mixture was cooled, acidified and partitioned between ethyl acetate and water. The organic phase was washed with water and brine and dried, then filtered through a bed of celite to obtain after removal of solvent and purification with flash silica gel chromatography to obtain 4"-(n-pentyloxy)-[1,1':4',1"-terphenyl]-4-carboxylic acid.

$^1$H NMR (400 MHz, DMSO-$d_6$) δ0.89 (t, 3H), 1.37 (m, 4H), 1.72 (m, 2H), 3.98 (t, 2H), 7.01 (d, 2H).

To a mixture of 4"-(n-pentyloxy)-[1,1':4',1"-terphenyl]-4-carboxylic acid (10.5 mmol) and dicyclohexylcarbodiimide (10.5 mmol) in ethyl acetate at 0° C. is added pentafluorophenol (11.5 mmol). The mixture is stirred at 25° C. for a period of 18 h, producing a precipitate. The mixture is filtered. The filtrate is washed with water and brine and dried with magnesium sulfate. The solvent is removed in vacuo to obtain pentafluorophenyl 4"-(n-pentytoxy)-[1,1':4',1"-terphenyl]-4-carboxylate, $C_{30}H_{23}F_5O_3$, M.W.=526.5.

Preparation of Alkoxy Biphenyl Side Chains.

The biphenylcarboxylic acid esters may be obtained through the following sequence of reactions illustrated as follows:

A. Preparation Of Octyloxybiphenylcarboxylic acid

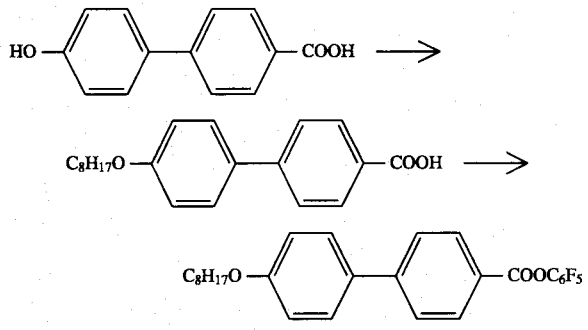

n-Octyl bromide (0.102 mol) is added to a solution of 4-(4-hydroxyphenyl)benzoic acid (0.102 mol) and 2.5N sodium hydroxide (0.102 mol) and the mixture stirred at 70° C. for a period of 18 hours. The reaction mixture is allowed to cool and then acidified to pH 3 and partitioned between ethyl acetate and water. The organic phase is washed with water and brine and the solvent then removed to obtain the 4'-n-octyloxy[1,1'-biphenyl]-4-ylcarboxylic acid, $C_{21}H_{23}O_3$, M.W. 326.4.

B. Preparation of pentafluorophenyl Ester

Pentafluorophenol (11.5 mmol) is added at 0° to a mixture of 10.5 mmol 4'-n-octyloxy[1,1'-biphenyl]-4-ylcarboxylic acid and 10.5 mmol of dicyclohexylcarbodiimide in ethyl acetate. The mixture is stirred at 25° C. for a period of 18 hours whereupon a precipitate is formed. The reaction mixture is filtered, the filtrate washed with water and brine and dried, the solvent removed in vacuo to obtain pentafluorophenyl 4'-n-octyloxy[1,1'-biphenyl]-4-ylcarboxylate, $C_{27}H_{25}F_5O_3$, M.W. 492.5.

Preparation Of AminoethyloxyBiphenyl Side chains

Preparation of 4'-(2-[4-Cyctohexylmethylpiperidin-1-yl]ethoxy)-[1,1'-biphenyl]-4-ylcarboxylic acid, Pentafluorophenyl Ester

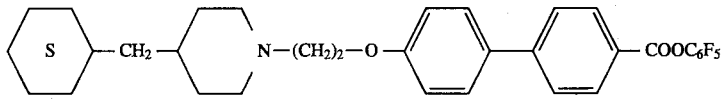

Part A: Preparation of 4-Cyclohexylmethylpiperidine

4-Benzylpiperidine is dissolved in glacial acetic acid containing $PtO_2$ (approximately 50 wt percent). A Paar hydrogenator is used and the reaction vessel is flushed with $H_2$ and pressurized to 3 atm. The mixture is shaken for sufficient time to give reduction of the aromatic ting to the fully saturated product which is determined by the uptake of 3 molar equivalents of $H_2$. The black solid is filtered and the acetic acid removed by evaporation under reduced pressure to obtain the product as an acetate salt.

Part B: Preparation of 1-(2-Hydroxyethyl)-4-cyclohexylmethylpiperidine

The product from Part A (1.0 eq) is dissolved in dichloromethane containing an equimolar amount of diisopropylethyl amine. Ethylene oxide (10 eq) is added and the mixture is stirred until starting material is consumed. The desired product is obtained by removal of the solvent in vacuo followed by purification by column chromatography.

Part C: Preparation of 4'-(2-[4-cyclohexylmethylpiperidine-1-yl]ethoxy)-[1,1'-biphenyl] -4-ylcarboxylic acid 4'-Hydroxy-[1,1'-biphenyl-4-ylcarboxylic acid methyl ester (1.0 eq) is dissolved in dichloromethane and triphenylphosphine (1.3 eq) and the hydroxyethyl compound (1.0 eq) from Part B is added. Next, diethyl azodicarboxylate (1.3 eq) is added and the mixture is stirred until starting material is consumed. The mixture is diluted with dichloromethane and washed with water. The organic layer is dried with MgSO$_4$ and filtered. The solvent is removed in vacuo and the residue is dissolved in ethanol. An excess of 3N sodium hydroxide is added and the mixture stirred for several hours. The reaction is neutralized with 2N HCl and is extracted with ethyl acetate. The ethyl acetate layer is dried with MgSO$_4$, filtered and the solvent vaporized under reduced pressure. The desired product is obtained in substantially pure form by column chromatography.

Part D: Preparation of the Pentafluorophenyl Ester

The carboxylic acid (1.0 eq) and dicyclohexylcarbodiimide (1.0 eq) are dissolved in ethyl acetate and the solution is cooled to 0° C. Pentafluorophenol (1.05 eq) is added, the ice bath then is removed and the reaction stirred at ambient temperature for 18–24 h. An equal volume of ether is added, the mixture is filtered and the solvent removed in vacuo. The product (MW=587.64) may be obtained in a sufficiently pure form to be utilized "as is" for nucleus acylation.

Preparation of 4'-(2-[4-Undecylpiperizin-1-yl]-ethoxy)[1,1'-biphenyl]-4-ylcarboxylic acid, Pentafluorophenyl Ester

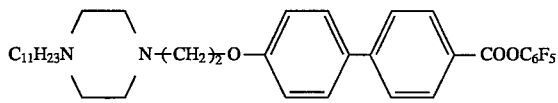

Part A: Preparation of 4-Undecylpiperazine

Excess piperazine (5 eq) and 1-bromoundecane (1.0 eq) are dissolved in dichloromethane and allowed to react overnight. The mixture is extracted with aqueous sodium bicarbonate and the organic layer dried with sodium sulfate. The mixture is filtered, the solvent removed in vacuo and the residue purified by column chromatography.

Part B: Preparation of 1-(2-Hydroxyethyl)-4-undecylpiperazine

The substituted piperazine above (1.0 eq) is dissolved in n-propanol and bromoethanol (1.0 eq) is added along with diisopropylethyl amine (1.1 eq). After several hours, the solvent is removed in vacuo and the residue dissolved in dichloromethane. The organic layer is washed with water and then aqueous sodium bicarbonate. The organic layer is dried with MgSO$_4$ and filtered. Removal of the solvent in vacuo is followed by purification by column chromatography.

Part C: Preparation of the Carboxylic Acid

The procedure is essentially the same as describe in Part C above except that the hydroxyethyl piperazine from above is substituted for the hydroxyethyl piperidine.

Part D: Preparation of the Pentafluorophenyl Ester

The procedure is identical to Part D from above except that piperazinyl-substituted-biphenyl carboxylic acid is used. The product (MW=646.75) may be obtained in a sufficiently pure form to be utilized "as is" in nucleus acylation.

---

What is claimed is:
1. A compound selected from the group consisting of
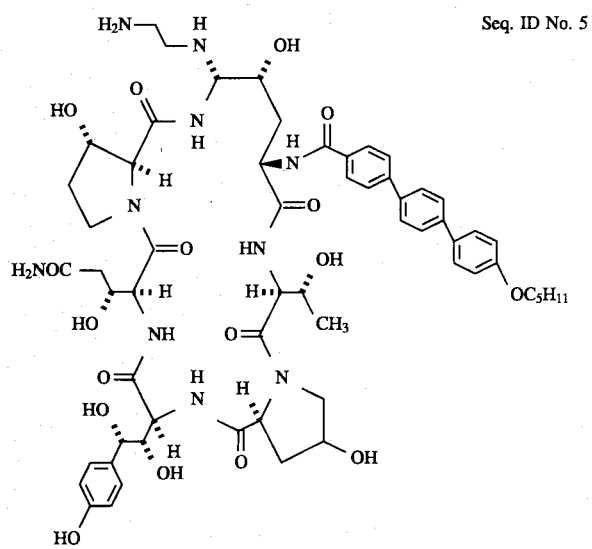
Seq. ID No. 5
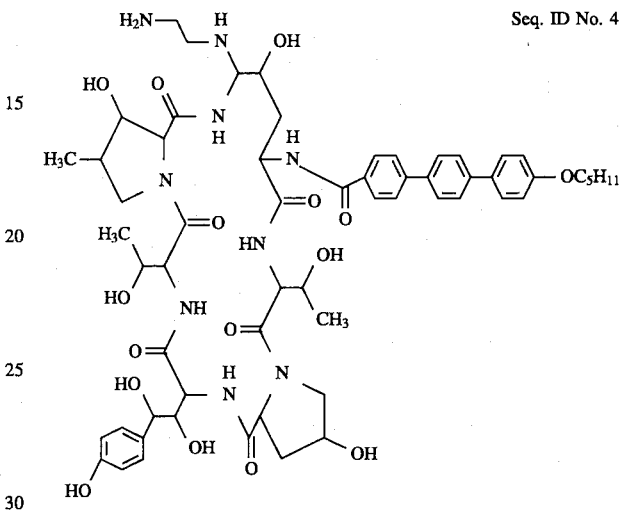
Seq. ID No. 4
-continued
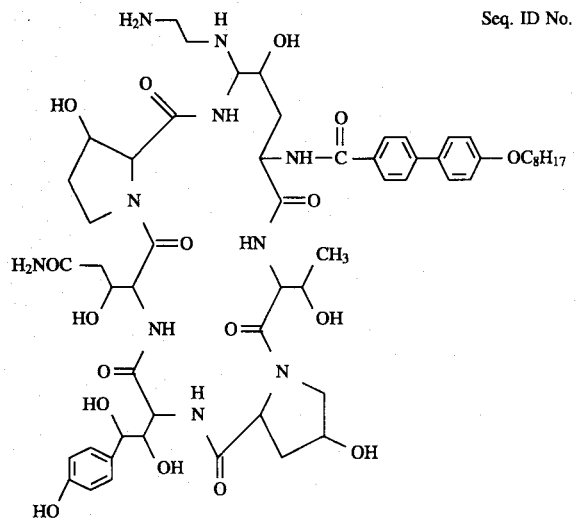
Seq. ID No. 5
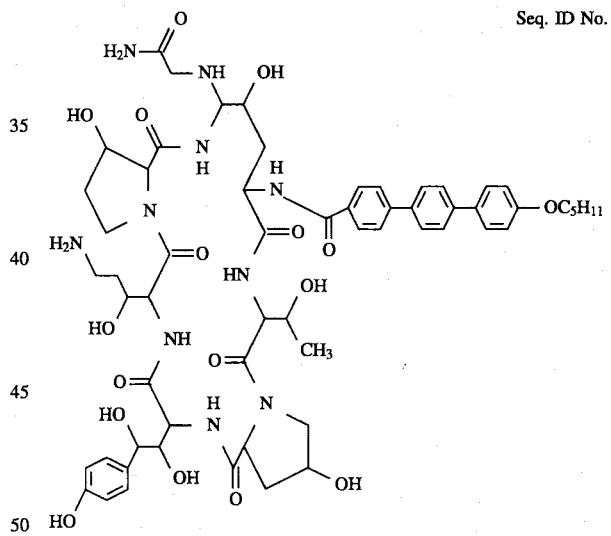
Seq. ID No. 7
and -continued

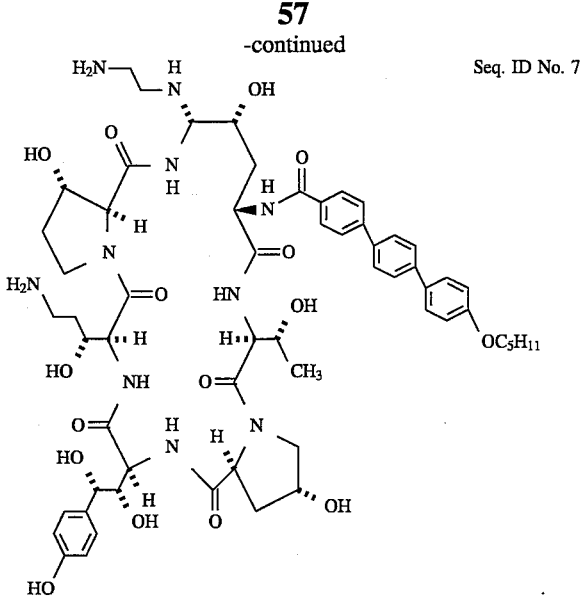

Seq. ID No. 7

2. An antibiotic composition comprising an antimicrobial amount of a compound of claim 1 in a pharmaceutically acceptable carrier.

3. A composition according to claim 2 in unit dosage form wherein the compound is present in an amount of 10 mg to 200 milligrams.

4. A method for treating mycotic infections comprising administering a therapeutic mount of a compound of claim 1 to a subject in need of therapy.

5. A method for treating *Pneumocystis carinii* infections which comprises administering a therapeutic amount of a compound as defined in claim 1.

* * * * *

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 1:

Xaa  Thr  Xaa  Xaa  Xaa  Xaa
        1                       5

( 2 ) INFORMATION FOR SEQ ID NO:2:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 2:

Xaa  Thr  Xaa  Xaa  Xaa  Xaa

```
                    1               5
```

( 2 ) INFORMATION FOR SEQ ID NO:3:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 3:

```
            Xaa  Thr  Xaa  Xaa  Xaa  Xaa
            1                    5
```

( 2 ) INFORMATION FOR SEQ ID NO:4:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 4:

```
            Xaa  Thr  Xaa  Xaa  Thr  Xaa
            1                    5
```

( 2 ) INFORMATION FOR SEQ ID NO:5:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 5:

```
            Xaa  Thr  Xaa  Xaa  Xaa  Xaa
            1                    5
```

( 2 ) INFORMATION FOR SEQ ID NO:6:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 6:

```
            Xaa  Thr  Xaa  Xaa  Xaa  Xaa
            1                    5
```

( 2 ) INFORMATION FOR SEQ ID NO:7:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:

(A) DESCRIPTION: PEPTIDE (x i) SEQUENCE DESCRIPTION: SEQ ID NO: 7:

```
Xaa  Thr  Xaa  Xaa  Xaa  Xaa
1                    5
```

(2) INFORMATION FOR SEQ ID NO:8:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (x i) SEQUENCE DESCRIPTION: SEQ ID NO: 8:

```
Xaa  Thr  Xaa  Xaa  Xaa  Xaa
1                    5
```

(2) INFORMATION FOR SEQ ID NO:9:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (x i) SEQUENCE DESCRIPTION: SEQ ID NO: 9:

```
Xaa  Thr  Xaa  Xaa  Xaa  Xaa
1                    5
```

(2) INFORMATION FOR SEQ ID NO:10:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (x i) SEQUENCE DESCRIPTION: SEQ ID NO: 10:

```
Xaa  Thr  Xaa  Xaa  Xaa  Xaa
1                    5
```

(2) INFORMATION FOR SEQ ID NO:11:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (x i) SEQUENCE DESCRIPTION: SEQ ID NO: 11:

```
Xaa  Thr  Xaa  Xaa  Xaa  Xaa
1                    5
```

(2) INFORMATION FOR SEQ ID NO:12:

(i) SEQUENCE CHARACTERISTICS:
(A) LENGTH: 6

(B) TYPE: AMINO ACID
            (C) STRANDEDNESS: Not Relevant
            (D) TOPOLOGY: CIRCULAR (i i) MOLECULE TYPE:
            (A) DESCRIPTION: PEPTIDE (x i) SEQUENCE DESCRIPTION: SEQ ID NO: 12:

Xaa  Thr  Xaa  Xaa  Xaa  Xaa
        1                   5

(2) INFORMATION FOR SEQ ID NO:13:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (i i) MOLECULE TYPE:
            (A) DESCRIPTION: PEPTIDE (x i) SEQUENCE DESCRIPTION: SEQ ID NO: 13:

Xaa  Thr  Xaa  Xaa  Xaa  Xaa
        1                   5

(2) INFORMATION FOR SEQ ID NO:14:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (i i) MOLECULE TYPE:
            (A) DESCRIPTION: PEPTIDE (x i) SEQUENCE DESCRIPTION: SEQ ID NO: 14:

Xaa  Thr  Xaa  Xaa  Thr  Xaa
        1                   5

(2) INFORMATION FOR SEQ ID NO:15:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (i i) MOLECULE TYPE:
            (A) DESCRIPTION: PEPTIDE (x i) SEQUENCE DESCRIPTION: SEQ ID NO: 15:

Xaa  Thr  Xaa  Xaa  Xaa  Xaa
        1                   5

(2) INFORMATION FOR SEQ ID NO:16:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (i i) MOLECULE TYPE:
            (A) DESCRIPTION: PEPTIDE (x i) SEQUENCE DESCRIPTION: SEQ ID NO: 16:

Xaa  Thr  Xaa  Xaa  Xaa  Xaa
        1                   5

( 2 ) INFORMATION FOR SEQ ID NO:17:

( i ) SEQUENCE CHARACTERISTICS:
    ( A ) LENGTH: 6
    ( B ) TYPE: AMINO ACID
    ( C ) STRANDEDNESS: Not Relevant
    ( D ) TOPOLOGY: CIRCULAR ( i i ) MOLECULE TYPE:
    ( A ) DESCRIPTION: PEPTIDE ( x i ) SEQUENCE DESCRIPTION: SEQ ID NO: 17:

Xaa  Thr  Xaa  Xaa  Xaa  Xaa
    1                  5

( 2 ) INFORMATION FOR SEQ ID NO:18:

( i ) SEQUENCE CHARACTERISTICS:
    ( A ) LENGTH: 6
    ( B ) TYPE: AMINO ACID
    ( C ) STRANDEDNESS: Not Relevant
    ( D ) TOPOLOGY: CIRCULAR ( i i ) MOLECULE TYPE:
    ( A ) DESCRIPTION: PEPTIDE ( x i ) SEQUENCE DESCRIPTION: SEQ ID NO: 18:

Xaa  Thr  Xaa  Xaa  Xaa  Xaa
    1                  5

( 2 ) INFORMATION FOR SEQ ID NO:19:

( i ) SEQUENCE CHARACTERISTICS:
    ( A ) LENGTH: 6
    ( B ) TYPE: AMINO ACID
    ( C ) STRANDEDNESS: Not Relevant
    ( D ) TOPOLOGY: CIRCULAR ( i i ) MOLECULE TYPE:
    ( A ) DESCRIPTION: PEPTIDE ( x i ) SEQUENCE DESCRIPTION: SEQ ID NO: 19:

Xaa  Thr  Xaa  Xaa  Xaa  Xaa
    1                  5

( 2 ) INFORMATION FOR SEQ ID NO:20:

( i ) SEQUENCE CHARACTERISTICS:
    ( A ) LENGTH: 6
    ( B ) TYPE: AMINO ACID
    ( C ) STRANDEDNESS: Not Relevant
    ( D ) TOPOLOGY: CIRCULAR ( i i ) MOLECULE TYPE:
    ( A ) DESCRIPTION: PEPTIDE ( x i ) SEQUENCE DESCRIPTION: SEQ ID NO: 20:

Xaa  Thr  Xaa  Xaa  Xaa  Xaa
    1                  5

( 2 ) INFORMATION FOR SEQ ID NO:21:

( i ) SEQUENCE CHARACTERISTICS:
    ( A ) LENGTH: 6
    ( B ) TYPE: AMINO ACID
    ( C ) STRANDEDNESS: Not Relevant
    ( D ) TOPOLOGY: CIRCULAR ( i i ) MOLECULE TYPE:
    ( A ) DESCRIPTION: PEPTIDE ( x i ) SEQUENCE DESCRIPTION: SEQ ID NO: 21:

Xaa Thr Xaa Xaa Xaa Xaa
   1         5

( 2 ) INFORMATION FOR SEQ ID NO:22:

( i ) SEQUENCE CHARACTERISTICS:
    ( A ) LENGTH: 6
    ( B ) TYPE: AMINO ACID
    ( C ) STRANDEDNESS: Not Relevant
    ( D ) TOPOLOGY: CIRCULAR ( i i ) MOLECULE TYPE:
    ( A ) DESCRIPTION: PEPTIDE ( x i ) SEQUENCE DESCRIPTION: SEQ ID NO: 22:

Xaa Thr Xaa Xaa Xaa Xaa
   1         5

( 2 ) INFORMATION FOR SEQ ID NO:23:

( i ) SEQUENCE CHARACTERISTICS:
    ( A ) LENGTH: 6
    ( B ) TYPE: AMINO ACID
    ( C ) STRANDEDNESS: Not Relevant
    ( D ) TOPOLOGY: CIRCULAR ( i i ) MOLECULE TYPE:
    ( A ) DESCRIPTION: PEPTIDE ( x i ) SEQUENCE DESCRIPTION: SEQ ID NO: 23:

Xaa Thr Xaa Xaa Xaa Xaa
   1         5

( 2 ) INFORMATION FOR SEQ ID NO:24:

( i ) SEQUENCE CHARACTERISTICS:
    ( A ) LENGTH: 6
    ( B ) TYPE: AMINO ACID
    ( C ) STRANDEDNESS: Not Relevant
    ( D ) TOPOLOGY: CIRCULAR ( i i ) MOLECULE TYPE:
    ( A ) DESCRIPTION: PEPTIDE ( x i ) SEQUENCE DESCRIPTION: SEQ ID NO: 24:

Xaa Thr Xaa Xaa Thr Xaa
   1         5

( 2 ) INFORMATION FOR SEQ ID NO:25:

( i ) SEQUENCE CHARACTERISTICS:
    ( A ) LENGTH: 6
    ( B ) TYPE: AMINO ACID
    ( C ) STRANDEDNESS: Not Relevant
    ( D ) TOPOLOGY: CIRCULAR ( i i ) MOLECULE TYPE:
    ( A ) DESCRIPTION: PEPTIDE ( x i ) SEQUENCE DESCRIPTION: SEQ ID NO: 25:

Xaa Thr Xaa Xaa Xaa Xaa
   1         5

( 2 ) INFORMATION FOR SEQ ID NO:26:

( i ) SEQUENCE CHARACTERISTICS:
    ( A ) LENGTH: 6
    ( B ) TYPE: AMINO ACID
    ( C ) STRANDEDNESS: Not Relevant (D) TOPOLOGY: CIRCULAR (ii) MOLECULE TYPE:
(A) DESCRIPTION: PEPTIDE (xi) SEQUENCE DESCRIPTION: SEQ ID NO: 26:

Xaa Thr Xaa Xaa Xaa Xaa
1               5

(2) INFORMATION FOR SEQ ID NO:27:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (xi) SEQUENCE DESCRIPTION: SEQ ID NO: 27:

Xaa Thr Xaa Xaa Xaa Xaa
1               5

(2) INFORMATION FOR SEQ ID NO:28:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (xi) SEQUENCE DESCRIPTION: SEQ ID NO: 28:

Xaa Thr Xaa Xaa Xaa Xaa
1               5

(2) INFORMATION FOR SEQ ID NO:29:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (xi) SEQUENCE DESCRIPTION: SEQ ID NO: 29:

Xaa Thr Xaa Xaa Xaa Xaa
1               5

(2) INFORMATION FOR SEQ ID NO:30:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (xi) SEQUENCE DESCRIPTION: SEQ ID NO: 30:

Xaa Thr Xaa Xaa Xaa Xaa
1               5

(2) INFORMATION FOR SEQ ID NO:31:

(i) SEQUENCE CHARACTERISTICS:
    (A) LENGTH: 6
    (B) TYPE: AMINO ACID
    (C) STRANDEDNESS: Not Relevant
    (D) TOPOLOGY: CIRCULAR (ii) MOLECULE TYPE:
    (A) DESCRIPTION: PEPTIDE (xi) SEQUENCE DESCRIPTION: SEQ ID NO: 31:

```
Xaa Thr Xaa Xaa Xaa Xaa
 1               5
```

(2) INFORMATION FOR SEQ ID NO:32:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 32:

```
Xaa Thr Xaa Xaa Xaa Xaa
 1               5
```

(2) INFORMATION FOR SEQ ID NO:33:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 33:

```
Xaa Thr Xaa Xaa Xaa Xaa
 1               5
```

(2) INFORMATION FOR SEQ ID NO:34:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 34:

```
Xaa Thr Xaa Xaa Thr Xaa
 1               5
```

(2) INFORMATION FOR SEQ ID NO:35:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 35:

```
          Xaa  Thr  Xaa  Xaa  Xaa  Xaa
          1                   5
```

( 2 ) INFORMATION FOR SEQ ID NO:36:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 36:

```
     Xaa  Thr  Xaa  Xaa  Xaa  Xaa
     1                   5
```

( 2 ) INFORMATION FOR SEQ ID NO:37:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 37:

```
     Xaa  Thr  Xaa  Xaa  Xaa  Xaa
     1                   5
```

( 2 ) INFORMATION FOR SEQ ID NO:38:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 38:

```
     Xaa  Thr  Xaa  Xaa  Xaa  Xaa
     1                   5
```

( 2 ) INFORMATION FOR SEQ ID NO:39:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 39:

```
     Xaa  Thr  Xaa  Xaa  Xaa  Xaa
     1                   5
```

( 2 ) INFORMATION FOR SEQ ID NO:40:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR (ii) MOLECULE TYPE:
   (A) DESCRIPTION: PEPTIDE
(xi) SEQUENCE DESCRIPTION: SEQ ID NO: 40:
   Xaa  Thr  Xaa  Xaa  Xaa  Xaa
   1              5